US012085530B2

(12) United States Patent
Abdolahad et al.

(10) Patent No.: US 12,085,530 B2
(45) Date of Patent: Sep. 10, 2024

(54) ELECTROMECHANICAL APPROACH FOR CANCER DETECTION

(71) Applicants: Mohammad Abdolahad, Tehran (IR); Ali Saeidi, Tehran (IR)

(72) Inventors: Mohammad Abdolahad, Tehran (IR); Ali Saeidi, Tehran (IR)

(73) Assignee: NANO HESGARSAZAN SALAMAT ARYA NCUBATION CENTER FOR MEDICAL EQUIPMENT AND DEVICES, Tehran (IR)

( * ) Notice: Subject to any disclaimer, the term of this patent is extended or adjusted under 35 U.S.C. 154(b) by 875 days.

(21) Appl. No.: 17/016,435

(22) Filed: Sep. 10, 2020

(65) Prior Publication Data

US 2021/0063341 A1 Mar. 4, 2021

Related U.S. Application Data

(63) Continuation-in-part of application No. 15/238,795, filed on Aug. 17, 2016, now Pat. No. 10,775,336.

(60) Provisional application No. 62/263,616, filed on Dec. 5, 2015.

(51) Int. Cl.
*G01N 27/327* (2006.01)
*C23C 14/16* (2006.01)
*G01N 27/02* (2006.01)
*G01N 27/28* (2006.01)
*G01N 33/483* (2006.01)

(52) U.S. Cl.
CPC ......... *G01N 27/3278* (2013.01); *C23C 14/16* (2013.01); *G01N 27/028* (2013.01); *G01N 27/283* (2013.01); *G01N 33/4833* (2013.01)

(58) Field of Classification Search
CPC ............ G01N 27/3278; G01N 27/028; G01N 27/283; G01N 33/48728; G01N 33/4833; G23C 14/16; C23C 16/4418; C23C 16/24; C23C 28/30; C23C 28/32; C23C 28/321; C23C 28/322; C23C 28/34; C25F 3/08
See application file for complete search history.

(56) References Cited

FOREIGN PATENT DOCUMENTS

WO WO-9850791 A1 * 11/1998 ....... G01N 33/48728

* cited by examiner

*Primary Examiner* — Michael L Hobbs
(74) *Attorney, Agent, or Firm* — Bajwa IP Law Firm; Haris Zaheer Bajwa

(57) ABSTRACT

An electromechanical system for detecting cancerous state of a single cell. The electromechanical system includes an aspirating mechanism, an electrical measurement mechanism, and a processing mechanism. The aspirating mechanism is configured to extract a single cell from a suspension of a plurality of suspended biological cells, hold the extracted single cell, and apply a mechanical aspiration to the held single cell by applying a suction force to the held single cell. The electrical measurement mechanism is configured to apply a set of electrical signals to the single cell before and after applying the mechanical aspiration and measure two sets of electrical responses from the held single cell corresponding to the applied set of electrical signals before and after applying the mechanical aspiration The processing mechanism, including a data processor, configured to detect cancerous state of the single cell based on a difference between the two sets of electrical responses.

18 Claims, 31 Drawing Sheets

ELECTROMECHANICAL APPROACH FOR CANCER DETECTION

CROSS REFERENCE TO RELATED APPLICATION

This application is a continuation-in-part of U.S. patent application Ser. No. 15/238,795, filed Aug. 17, 2016, and entitled "AN ELECTROMECHANICAL APPROACH FOR CANCER DETECTION", now issued as U.S. Pat. No. 10/775,336, which takes priority from U.S. Provisional Patent Application Ser. No. 62/263,616 filed Dec. 05, 2015, entitled "A SINW-ECIS BIOSENSOR", which are both incorporated by reference herein in their entirety.

TECHNICAL FIELD

The present application generally relates to a tungsten (W) supported silicon nanotub- (SiNT) based electrical probe (designated hereinafter as "SiNT/W probe"), a method for fabrication thereof, and applications thereof in detecting cancerous state of a single cell.

BACKGROUND

Cancer is recognized as a type of disease that affects many biochemical, electrical, and mechanical functions of a cell. Cytoskeletal alterations, damping of electrodynamic microtubule oscillations, diminution of dielectric properties of the membrane, and disruption in the ion channel activity are some of the considerable mechanical and electrical alterations in cells during cancerous transformation.

Highly accurate methods for monitoring such alterations in single cells, such as electrical, mechanical, and electro-optical monitoring of single cells may detect cancerous transformation in its early stages. In case of electrical recording, high spatial resolution contacts between electrical probes and single cells and also non-invasive recording are critical for both fundamental biophysical studies and disease monitoring; particularly for the bioelectrical signals, which are weaker than action potentials.

Nanoscale electrical probes (e.g., conductive silicon nanowires and silicon nanotubes (SiNT)) have opened new fields of investigation, leading to the emergence of possible future applications in cell bioelectrical and electrophysiological studies. Recently, the nanostructured probe-based electrical recording methods have been applied solely for action potential measurements outside the cell of some special types of electrically active cells with sharp responses, such as neurons and cardiomyocytes.

Therefore, there is a need for a label-free cancer diagnosis or cancer progression detection method with single-cell resolution using non-invasive devices or instruments capable of measuring intracellular bioelectrical responses, even minor electrical variations for a wide range of cell types.

SUMMARY

In one general aspect of the present disclosure, an electromechanical system for detecting cancerous state of a single cell is disclosed. The electromechanical system may include an aspirating mechanism, an electrical measurement mechanism, and a processing mechanism. The aspirating mechanism may be configured to extract a single cell from a suspension of a plurality of suspended biological cells, hold the extracted single cell, and apply a mechanical aspiration to the held single cell by applying a suction force to the held single cell. The electrical measurement mechanism may be configured to apply a set of electrical signals to the single cell before and after applying the mechanical aspiration, measure a first set of electrical responses from the held single cell corresponding to the applied set of electrical signals before the mechanical aspiration, and measure a second set of electrical responses from the mechanically aspirated single cell corresponding to the applied set of electrical signals before the mechanical aspiration. The processing mechanism, that may include a data processor, may be configured to detect cancerous state of the single cell based on a difference between the first set of electrical responses and the second set of electrical responses.

In an exemplary embodiment, the biological cells may include a plurality of cells with elastic cell membranes. In an exemplary embodiment, the biological cells may include at least one of epithelial cells, endothelial cells, mesenchymal cells, and combinations thereof.

In an exemplary implementation, the set of electrical signals may include a set of electrical voltages of 40 mV at a set of frequency values in a range between 100 Hz and 100 KHz. In an exemplary implementation, each of the first set of electrical responses and the second set of electrical responses may include a set of at least one of electrical impedance values, electrical phase values, and combinations thereof.

In an exemplary implementation, the data processor may be configured to receive the first set of electrical responses and the second set of electrical responses from the electrical measurement mechanism, calculate the difference between the first set of electrical responses and the second set of electrical responses by calculating a set of difference values between each two respective values of the first set of electrical responses and the second set of electrical responses, and detect the single cell to be cancerous responsive to the calculated difference between the first set of electrical responses and the second set of electrical responses being near zero.

In an exemplary implementation, the aspirating mechanism may include an electrically activated micropipette and a liquid reservoir. The electrically activated micropipette may include a nozzle at a first end of the electrically activated micropipette. The nozzle may be configured to transfer the mechanical aspiration to the held single cell. The electrically activated micropipette may be configured to extract the single cell from the suspension of the plurality of suspended biological cells, hold the extracted single cell, and act as an electrical ground potential for the electrical measurement mechanism. The liquid reservoir may be connected to a second end of the electrically activated micropipette, and the liquid reservoir may be configured to function as a pressure source for the mechanical aspiration.

In an exemplary implementation, the electrically activated micropipette may include a micropipette and an electrical conductive layer that may be coated on outer surface of the nozzle. In an exemplary implementation, the electrical conductive layer may include at least one of gold (Au), titanium (Ti), platinum (Pt), and combinations thereof. In an exemplary implementation, the micropipette may be made of at least one of glass, quartz, plastic, and combinations thereof.

In an exemplary implementation, the electrically activated glass micropipette may be assembled on a microinjection microscope, and the liquid reservoir may include a movable water reservoir of the microinjection microscope. In an exemplary implementation, the movable water reservoir may be configured to move downward to function a suction pressure for the mechanical aspiration.

In an exemplary implementation, the electrical measurement mechanism may include an electrical probe and a signal controlling system. The electrical probe may be configured to connect to the held single cell. The signal controlling system that may be connected to the electrical probe, may be configured to apply an electrical signal to the held single cell via the electrical probe and acquire an electrical response corresponding to the applied electrical signal from the held single cell via the electrical probe.

In an exemplary implementation, the electrical probe may include a tungsten microwire with a diameter less than 500 μm with a sharpened tip section, a catalyst layer formed on the sharpened tip section, an array of nanotube electrodes vertically aligned on the catalyst layer, and a gold layer coated over the array of nanotube electrodes. In an exemplary embodiment, the sharpened tip section may include a sharp pointed tip with a diameter of 200 nm or less. In an exemplary embodiment, the array of nanotube electrodes may include a plurality of doped silicon nanotubes (SiNTs) that may include a long free-end silicon nanotube located on the sharp pointed tip. In an exemplary embodiment, the long free-end silicon nanotube may be longer than remaining SiNTs of the plurality of doped SiNTs, and may be configured to connect with and penetrate into the held single cell. In an exemplary embodiment, the gold layer may be coated over the plurality of doped SiNTs. In an exemplary embodiment, the electrical probe may be assembled on a microinjection microscope.

In an exemplary embodiment, the catalyst layer may include a catalyst bilayer, which may include a nickel layer over a gold layer. In an exemplary embodiment, the catalyst layer may include the nickel layer with a thickness in a range between 10 nm and 40 nm over the gold layer with a thickness in a range between 1 nm and 4 nm. In an exemplary embodiment, the gold layer coated over the plurality of doped SiNTs may have a thickness of 5 nm or less. In an exemplary embodiment, the plurality of doped SiNTs may include a plurality of doped SiNTs with phosphorus.

In an exemplary implementation, the signal controlling system may include an AC signal source and a data acquisition module. In an exemplary implementation, the AC signal source may be configured to apply the electrical signal to the electrical probe. In an exemplary implementation, the data acquisition module may be configured to acquire the electrical response corresponding to the applied electrical signal from the electrical probe and send the electrical response to the data processor. In an exemplary implementation, the AC signal source may be configured to apply a voltage of 40 mV in a frequency range between 100 Hz and 100 KHz to the electrical probe.

DETAILED DESCRIPTION

The following detailed description is presented to enable a person skilled in the art to make and use the application. For purposes of explanation, specific nomenclature is set forth to provide a thorough understanding of the present application. However, it will be apparent to one skilled in the art that these specific details are not required to practice the application. Descriptions of specific applications are provided only as representative examples. Various modifications to the preferred implementations will be readily apparent to one skilled in the art, and the general principles defined herein may be applied to other implementations and applications without departing from the scope of the application. The present application is not intended to be limited to the implementations shown, but is to be accorded the widest possible scope consistent with the principles and features disclosed herein.

Disclosed herein is an exemplary nanostructured electrical probe (a tungsten- (W-) supported silicon nanotube-(SiNT-) based electrical probe (SiNT/W probe)) and an exemplary method for fabrication thereof. The probe may be considered for a non-invasive measurement of electrical responses of a cell.

In an aspect, the present disclosure describes an exemplary electromechanical method to detect changes in the electrical properties of a single cell, between normal and cancerous states during a mechanical deformation. The method is based on the role of actin microfilaments within a cell in modulation of the ion channel activity and consequently based on the electrical response (e.g. electrical impedance, phase, etc.) of a cell during a mechanical deformation, such as mechanical aspiration. In some aspects, the method may be considered as a new label-free electromechanical cancer diagnosis and cancer progression monitoring method with a single-cell resolution.

Figure 1:
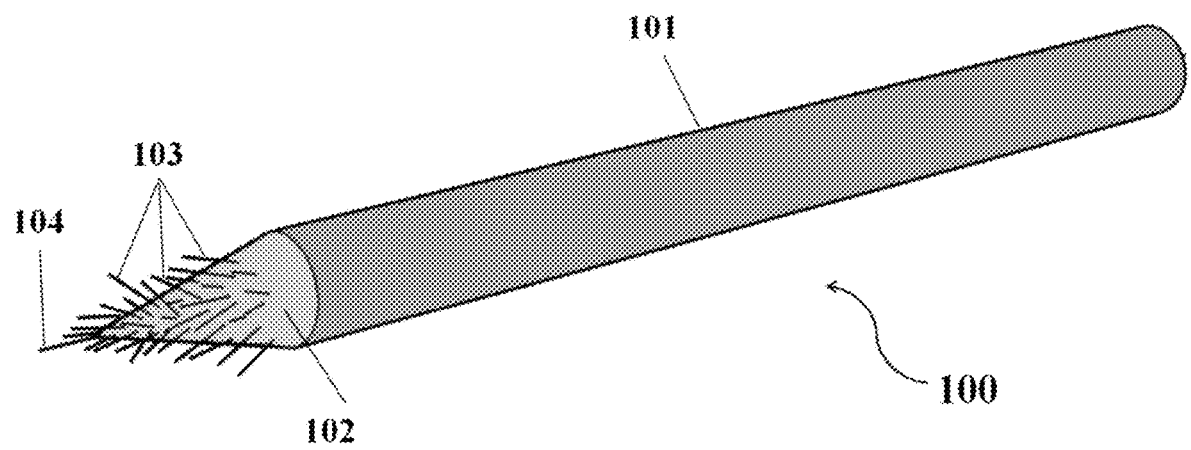
FIG. 1 is a schematic of one example of a SiNT/W probe, consistent with one or more exemplary embodiments of the present disclosure.

FIG. 1 illustrates a schematic of one example of a SiNT/W probe 100, consistent with one or more exemplary embodiments of the present disclosure, which may be configured for measuring an electrical response from a biological cell. Referring to the implementation shown in FIG. 1, the SiNT/W probe 100 may include a tungsten (W) microwire 101 with a sharpened tip 102 that may be coated with a catalyst bilayer and a plurality of silicon nanotube (SiNTs) electrodes 103 vertically aligned on the catalyst bilayer. The SiNTs 103 may be configured to connect or attach to a biological cell and measure an electrical response of the biological cell that is in contact with the electrodes. Accordingly, a long free-end SiNT 104 may be used among other SiNTs within the array. The long free-end SiNT 104 may be configured for connecting to a biological cell and penetrating the biological cell for further electrical measurement purposes according to one or more aspects of the present disclosure.

As used herein, a microwire may be a fine wire with a circular cross-section and a diameter less than 2000 μm. The microwire 101 may be, for example a tungsten (W) microwire. In certain examples, the tungsten (W) microwire 101 may have a diameter less than about 500 μm. A sharpened tip of the sharpened tip section 102 of the tungsten (W) microwire where the long free-end SiNT 104 may be connected may have a diameter of about 200 nm.

In some exemplary implementations, the catalyst layer may include a catalyst bilayer. The catalyst bilayer, as used herein, is defined as a double-layered catalyst with one layer of a first catalyst coated on another layer of a second catalyst. The catalyst bilayer may include a layer of Nickel (Ni) with a thickness of, for example about 10 nm to about 40 nm over a layer of gold (Au) with a thickness of, for example about 1 nm to about 4 nm forming a catalyst bilayer (Ni—Au).

In an implementation, the array of nanotubes 103 may include a plurality of vertically-aligned silicon nanotubes (SiNTs) that may be grown on the catalyst bilayer. The SiNTs may have a thickness or diameter of, for example less than about 100 nm.

Figure 2:
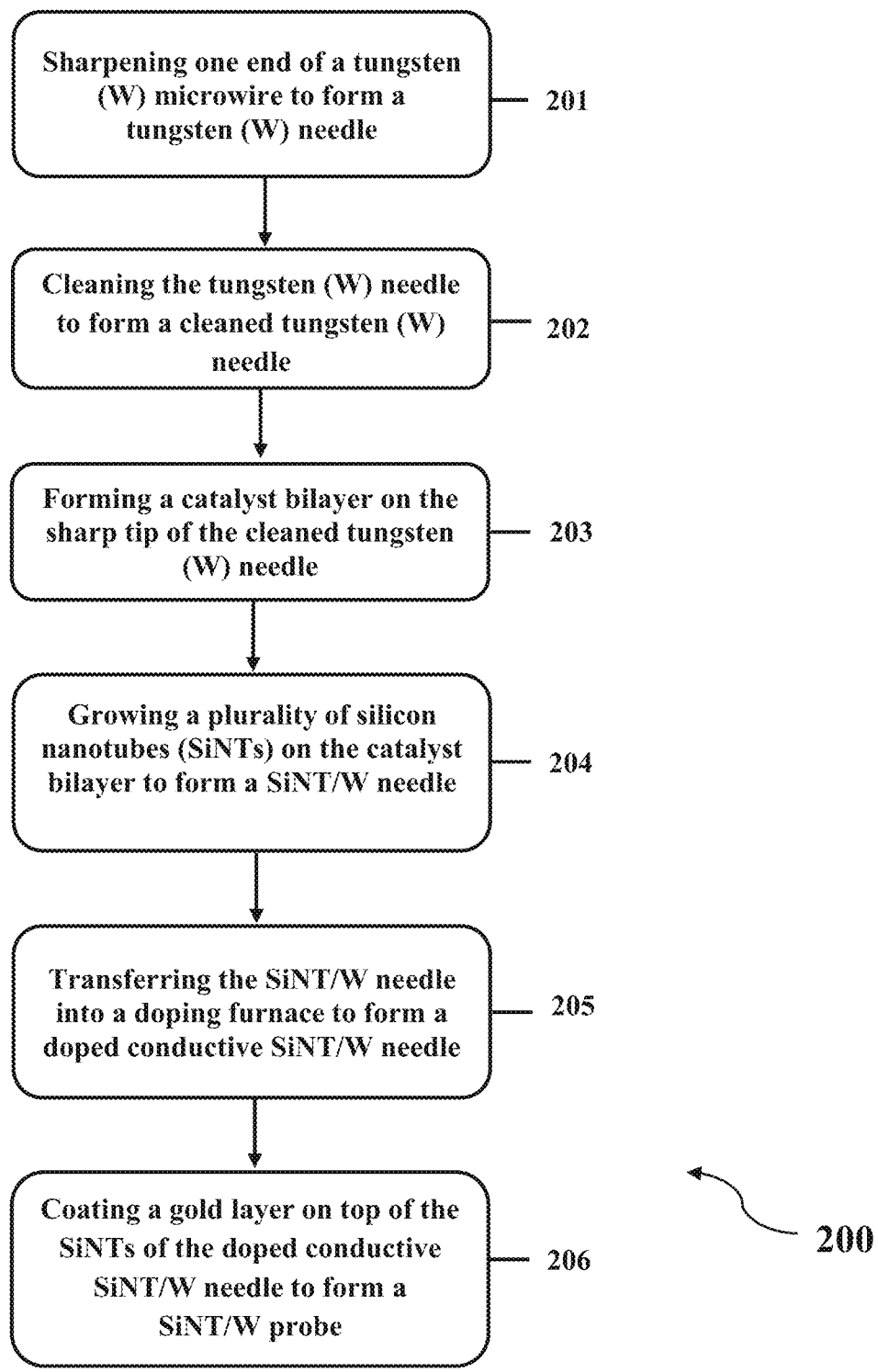
FIG. 2 illustrates an example method for fabricating a SiNT/W probe, consistent with one or more exemplary embodiments of the present disclosure.

FIG. 2 illustrates an example of a method 200 for fabricating the SiNT/W probe 100, consistent with one or more exemplary embodiments of the present disclosure. The method 200 may include the steps of: first, sharpening one end of a tungsten (W) microwire to form a tungsten (W) needle having a sharp pointed tip (step 201); second, cleaning the tungsten (W) needle to obtain a cleaned tungsten (W) needle (step 202); third, forming a catalyst bilayer on the sharpened tip of the cleaned tungsten (W) needle (step 203); fourth, growing a plurality of silicon nanotubes (SiNTs) on the catalyst bilayer to form a SiNT/W needle (step 204), fifth, transferring the SiNT/W needle into a doping furnace to form a doped conductive SiNT/W needle (step 205); and sixth, coating a gold layer on top of the SiNTs of the doped conductive SiNT/W needle (step 206).

Figure 3:
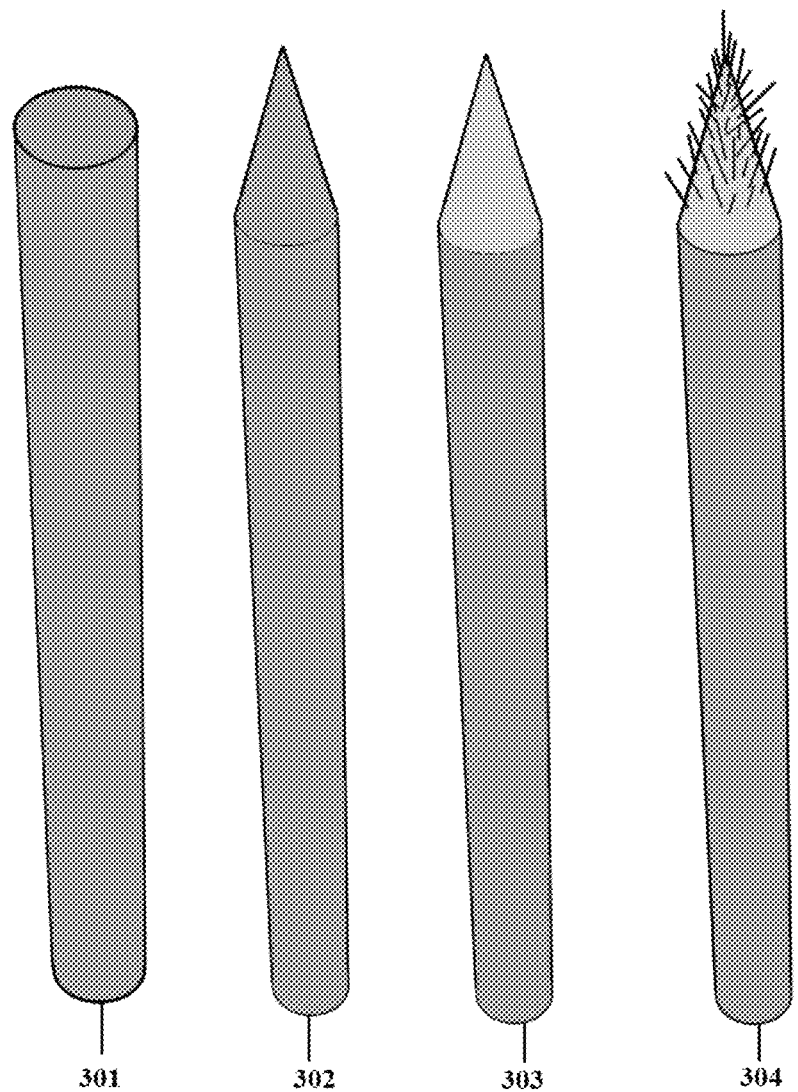
FIG. 3 is a schematic of one example of a tungsten (W) microwire, a tungsten (W) needle, and a cleaned tungsten (W) needle with a catalyst bilayer on the sharp tip and a SiNT/W needle, consistent with one or more exemplary embodiments of the present disclosure.

Referring to the first step 201, an initially supplied tungsten (W) microwire may be sharpened from one end, for example via an electrochemical etching process to form a tungsten (W) needle having a sharp pointed tip. FIG. 3 shows four schematics of one example of the initially supplied tungsten (W) microwire 301, the tungsten (W) needle 302, and the cleaned tungsten (W) needle having a catalyst bilayer on the sharp tip 303 and the SiNT/W needle 304 during the fabrication process, consistent with one or more exemplary embodiments of the present disclosure. Referring to FIG. 3, a schematic of one example of a tungsten (W) microwire 301 and the obtained tungsten (W) needle 302 after step 201 is illustrated.

Moving on to the second step 202, cleaning the tungsten needle may be carried out with immersing the tungsten needle in a cleaning solution, for example, a solution of acetone and buffer HF.

Moving on to the third step 203, the catalyst bilayer may be formed via a two-step deposition process, using, for example, an electron beam coating system via placing the needle in a position in which the top of the needle can be located in front of a target plume. The formation of the catalyst bilayer may include two steps of: first, holding the cleaned tungsten needle under a gold plume to coat a layer of gold on the sharp tip to form a first catalyst layer; and second, holding the cleaned tungsten needle having the first catalyst layer under a Nickel plume to coat a layer of nickel over the first catalyst layer to yield a catalyst bilayer (Ni—Au). Accordingly, a thin layer of gold, with a thickness ranging, for example from about 1 nm to about 4 nm may be coated on top of the sharp tip. Subsequently, a layer of nickel with a thickness ranging, for example from about 10 nm to about 40 nm may be coated over the gold layer. Referring to FIG. 3, a schematic of a tungsten needle 303 having a catalyst bilayer formed over its sharpened tip is illustrated.

Moving on to the fourth step 204, the SiNTs may be grown via a vapor-solid-liquid (VLS) process using a low-pressure chemical vapor deposition (LPCVD) chamber. The VLS process may be carried out by the assistance of, for example $H_2$ and $SiH_4$ gases at a temperature in a range of about 400° C. to about 600° C. and at a pressure of about 1 mTorr. An example of the obtained SiNT/W needle 304 from step 204 is schematically illustrated in FIG. 3.

Moving on to the fifth step 205, the doping step may be carried out by an element of group five of the periodic table, for example, phosphorous. In an implementation, the doping step may be carried out in a phosphorous doping furnace. The SiNT/W needle may be held in the phosphorous doping furnace at a temperature of, for example about 700° C. for about 10 minutes.

Moving on to the final step 206, the gold layer may be coated over the SiNTs via a sputtering system. The thickness of the gold layer may be, for example about 5 nm.

In another aspect, a single-cell-based electromechanical method for cancerous state detection of a single biological cell is described. The biological cell may be a biological cell having an elastic cell membrane with a defined membrane elasticity, for example, epithelial, endothelial, or mesenchymal cells. This method may be used, for example, for cancer diagnosis, detecting cancer transformation or progression, detecting cancer cells among biological cells, investigating metastatic stage, or generally for cancerous state determination of a malignant tissue.

Figure 4:
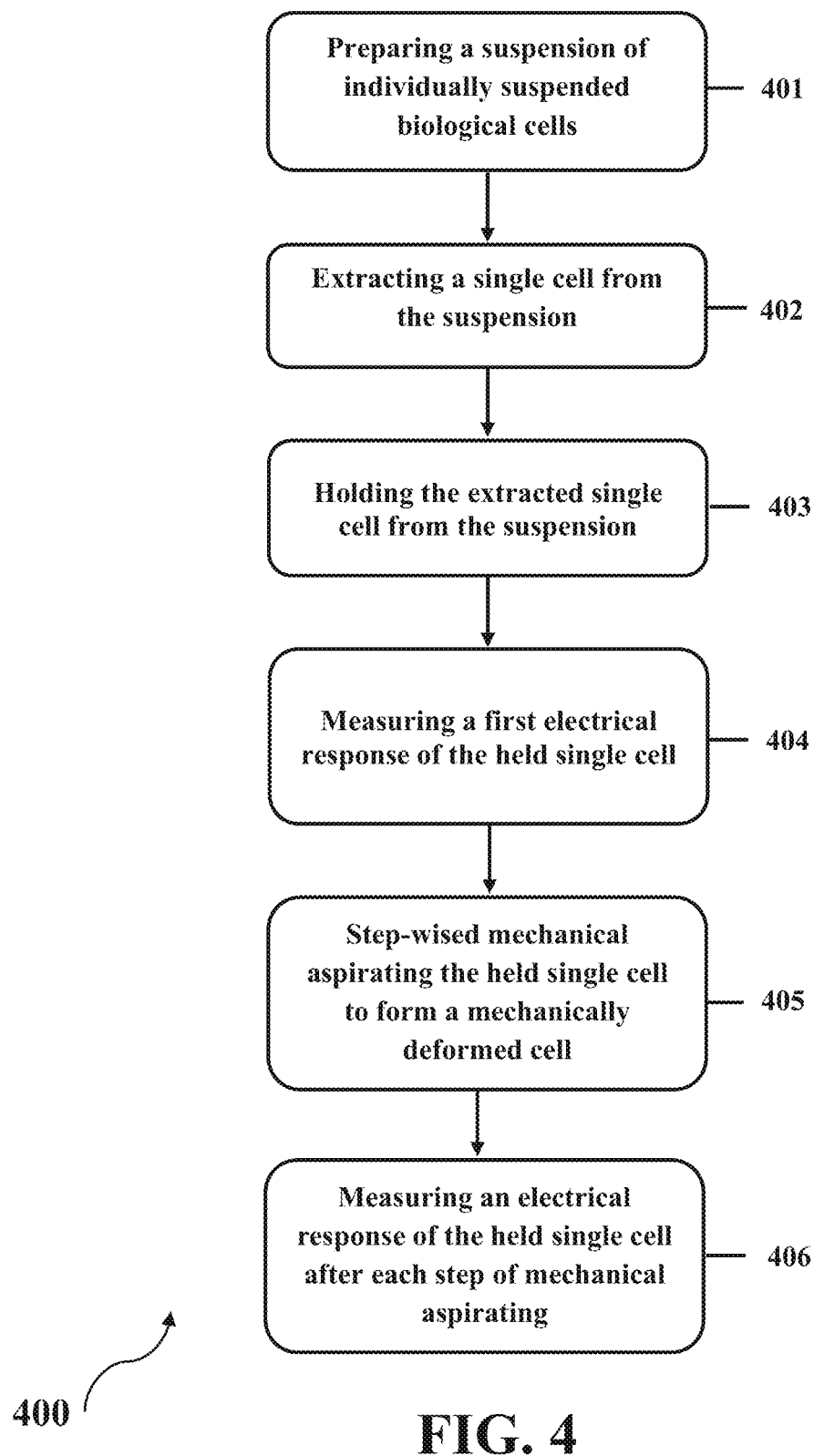
FIG. 4 illustrates an example of a single-cell-based electromechanical method for cancerous state detection, consistent with one or more exemplary embodiments of the present disclosure.

FIG. 4 shows an example of a method 400 for detecting the cancerous state of a single biological cell, consistent with one or more exemplary embodiments of the present disclosure. The method 400 may include steps of: first, preparing a suspension of individually suspended biological cells (step 401), second, extracting a single cell from the suspension (step 402), third, holding the extracted single cell from the suspension (step 403), fourth, measuring a first electrical response of the held single cell (step 404); fifth, step-wised mechanical aspirating the held single cell to form a mechanically deformed cell (step 405), and sixth, measuring an electrical response of the held single cell after each step of the mechanical aspirating (step 406).

In step 401, a suspension of biological cells including individual cells that are distributed within the suspension may be prepared via a process with steps of, culturing a plurality of biological cells onto a substrate; washing the cultured cells, trypsinizing the cultured cells to detach the cultured cells from the substrate and form a solution, and centrifuging the solution to separate a cell suspension that includes individually suspended biological cells. Accordingly, a plurality of biological cells may be cultured onto a substrate, for example a glass substrate. The cells may be cultured in a culture medium, for example, a Roswell Park Memorial Institute-1640 (RPMI-1640) medium. The culture medium may be supplemented with a serum-supplement, for example, Fetal bovine serum (FBS) including Fetal bovine with an amount of about 5% and the culture medium may be further supplemented with an antibiotic, for example, penicillin/streptomycin with an amount of about 1%. Then, the cultured cell may be washed with a buffer solution, for example, a Phosphate-buffered saline (PBS) solution to remove the remained cultured media and supplements from the cultured cells. Subsequently, the cultured and washed cells may be trypsinized by assistance of adding a solution including trypsin and EDTA to the cultured cells in order to detach the cultured cells from the substrate and form a solution including the cells. Finally, the obtained solution including the cultured cells may be centrifuged to discard the trypsinizing solution and separate a cell suspension including individually suspended biological cells.

Referring to second step 402 and subsequently, third step 403, a single cell may be extracted from the suspension and held for a while by assistance of an electrically activated micropipette. The electrically activated micropipette may be a glass micropipette with a diameter in a range of about 4.5 μm to about 5 μm, which may be coated with an electrically conductive layer, for example, a gold (Au) layer. The gold (Au) layer may be coated with a thickness of, for example about 10 nm over the glass micropipette via, for example a sputtering system.

Moving on to step 404, an electrical response of the held cell, for example, an electrical impedance of the cell membrane of the held cell may be measured using an electrical probe connected to the cell. The electrical probe may include a SiNT/W probe, designed and fabricated pursuant to the teachings of the present disclosure.

Moving on to step 405, the held single cell can be aspirated by assistance of the same electrically activated micropipette, which was used before for extracting step 402 and holding step 403. The electrically-activated micropipette may be assembled on a microinjection microscope to supply the electrically activated micropipette displacements needed in steps 402 and 403. In addition, the negative and positive pressure for aspirating the single cell may be applied to the glass micropipette by assistance of a movable water reservoir of the microinjection microscope. Displacing the water reservoir up or down leads to a suitable pressure to pull in or force away the cell. Furthermore, a micromanipulator may be utilized to adjust each micropipette position. Also, the aspirated leading edge of the cell surface may be monitored using an inverted microscope equipped with a digital camera assembled on the microinjection microscope.

Moving on to step 406, an electrical response of the held single cell after each step of mechanical aspirating of step 405 may be measured. Then, the cancerous state of the single cell may be determined based on the changes of the electrical response measured in step 404 and the electrical responses measured in step 406. Since, the electrical properties of a normal or healthy cell, for example electrical impedance of the cell membrane may be affected significantly by the mechanical properties of the cell, sharp and significant changes in the measured electrical responses from the single cell after cell mechanical deformation may indicate that the extracted single cell from the suspension is a healthy cell. While, no or small alterations in electrical responses measured during mechanical deformation may indicate that the selected and processed single cell via the method 400, pursuant to the teachings of the present disclosure is a cancer cell.

Figure 5A:
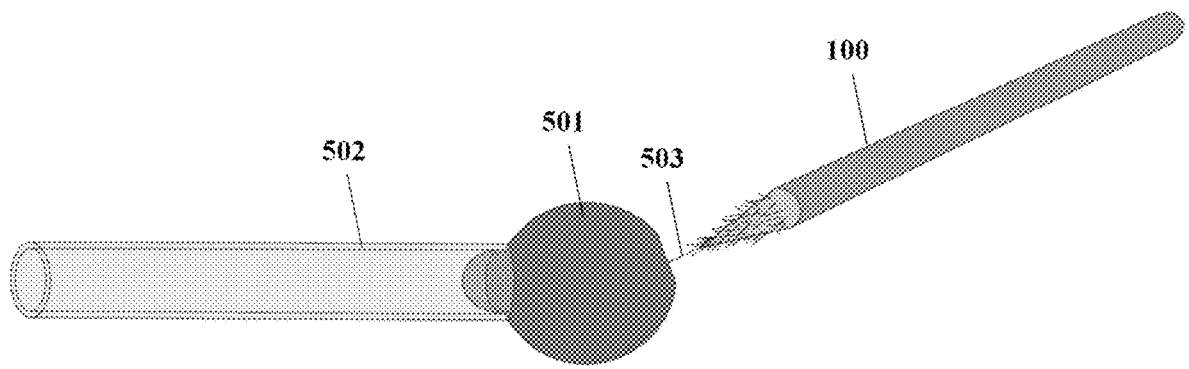
FIG. 5A is a schematic of an example single biological cell held and aspirated by assistance of an electrically activated micropipette and connected to a SiNT/W probe, consistent with one or more exemplary embodiments of the present disclosure.

FIG. 5A shows a schematic of an example of a single biological cell 501, which is extracted from a suspension including individually suspended cells, consistent with one or more exemplary embodiments of the present disclosure. Cell 501 is held and aspirated by assistance of an electrically activated micropipette 502 and it is in contact with a silicon nanotube (SiNT) 503 of a SiNT/W probe similar to a silicon nanotube (SiNT) 104 described hereinabove. SiNT 503 is a long free-end SiNT among the SiNTs array that is formed over the sharpened tip of the probe.

It should be understood that the structure changes in actin microfilament network of a cell due to a mechanical force may be a criterion for diagnosis between cancerous and healthy cells as well as between benign and metastatic cells. For example, a mechanical aspiration mechanism applied on a healthy or benign cell may cause a significant alteration in actin microfilament configuration and subsequently a significant change in an electrical response of the cell, for example electrical impedance or phase. While, a similar mechanical aspiration may not cause any observable change in such electrical responses in case of a cancerous or metastatic cell.

Figure 5B:
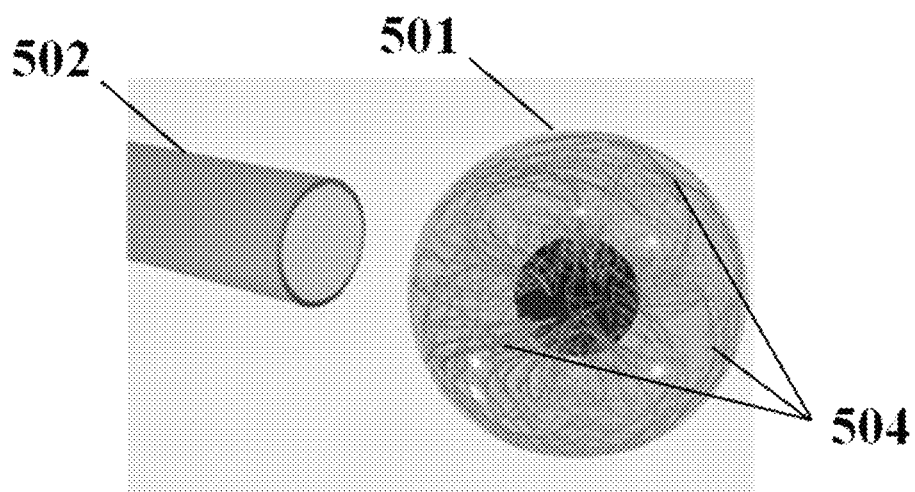
FIG. 5B is a schematic of actin microfilament distribution for an example of a non-aspirated cell, consistent with one or more exemplary embodiments of the present disclosure.
Figure 5C:
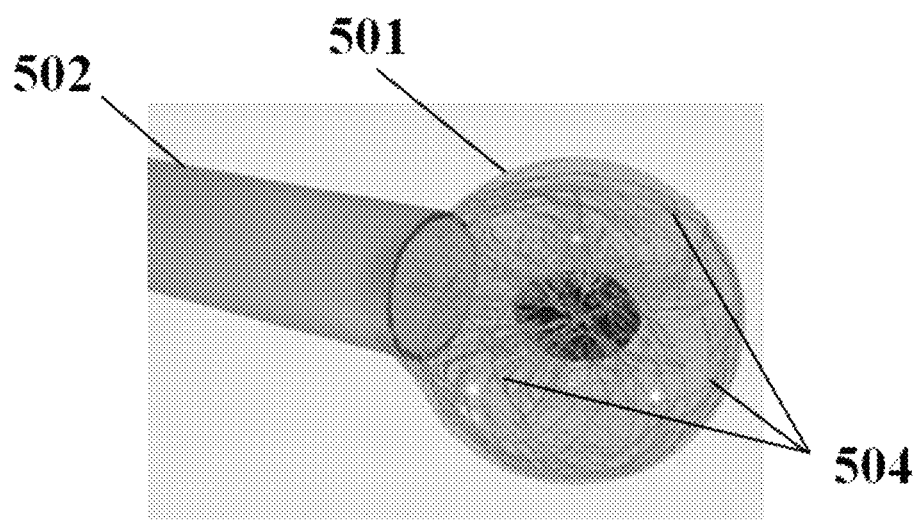
FIG. 5C is a schematic of actin microfilament distribution for an example of an aspirated cell, consistent with one or more exemplary embodiments of the present disclosure.

Accordingly, FIG. 5B shows a schematic of the actin microfilament configuration and distribution for a non-aspirated cell illustrating the electrically activated micropipette 502 near the single cell 501 as described hereinabove and a schematically actin microfilament distribution 504 of the cell, consistent with one or more exemplary embodiments of the present disclosure. Correspondingly, FIG. 5C shows a similar schematic actin microfilament configuration and distribution for an aspirated cell, consistent with one or more exemplary embodiments of the present disclosure.

In another aspect, an electromechanical system for detecting cancerous state of a single cell is described. The system may include a first aspirating mechanism to extract and hold a single cell and apply a mechanical aspiration to the single cell; and a second electrical measurement mechanism to measure an electrical response of the single cell. The cancerous state of the single cell may be detected based on the changes of the measured electrical responses.

Figure 6:
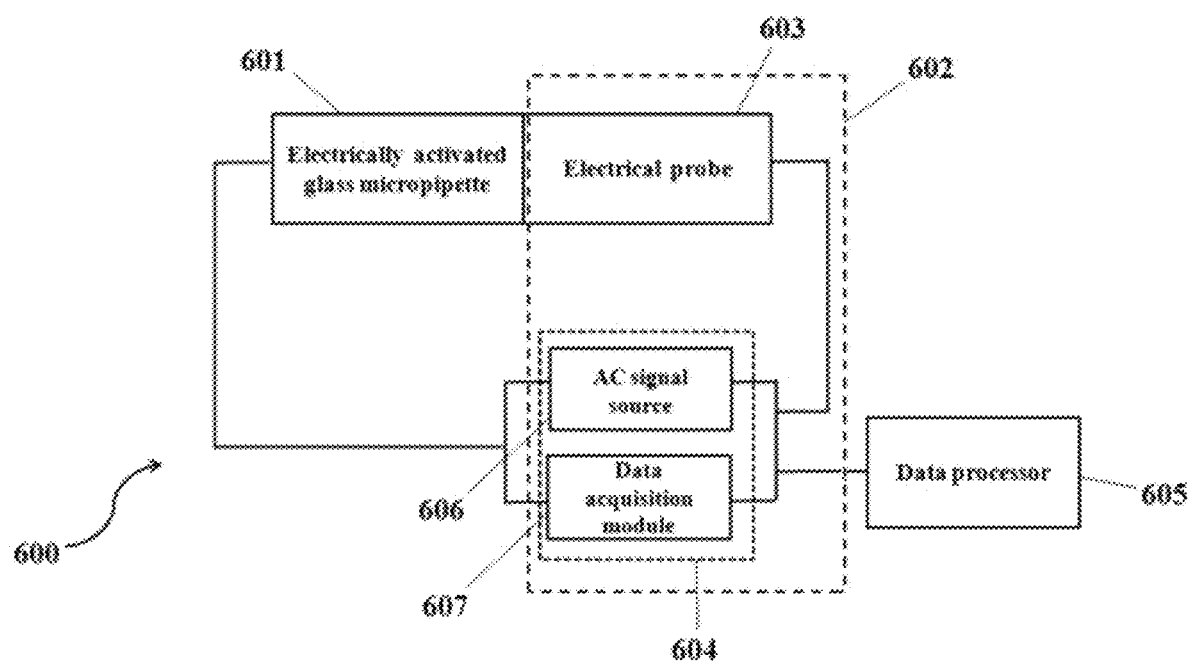
FIG. 6 illustrates an example of an electromechanical system for detecting cancerous state of a single cell, consistent with one or more exemplary embodiments of the present disclosure.

FIG. 6 illustrates an example of an electromechanical system 600, configured to detect cancerous state of a single cell, consistent with one or more exemplary embodiments of the present disclosure. The electromechanical system 600 may be utilized to implement the method 400 of FIG. 4 for detecting cancerous state of a single cell as described above. Exemplary system 600 may include an aspirating mechanism 601 configured to extract and hold a single cell and then applying a mechanical aspiration to the single cell and an electrical measurement mechanism 602 configured to measure an electrical response of the single cell. In an implementation, the aspirating mechanism 601 may include an electrically activated glass micropipette (similar to electrically activated micropipette 502) with two ends, which is coated with a gold layer. The electrically activated glass micropipette may be assembled on a microinjection microscope from one end, while having a nozzle at the other end to apply and transfer the mechanical aspiration to the single cell.

Referring to FIG. 6, the electrical measurement mechanism 602 may include an electrical probe 603 configured to be connected to the held cell by the electrically activated glass micropipette for electrical measurements, a signal controlling system 604 configured for applying an electrical signal to the extracted and held single cell connected to the electrical probe 603 and acquiring the corresponding electrical response of the extracted and held single cell connected to the electrical probe 603, and a data processor 605 configured for recording and analyzing the electrical response in order to detect the cancerous state of the single cell. The electrical probe 603 may include a tungsten-supported silicon nanotube-based (SiNT/W) probe assembled on a microinjection microscope opposite to the electrically activated glass micropipette 502 to connect and penetrate a long free-end SiNT 503 to the single cell held by the electrically activated glass micropipette 502.

With further reference to FIG. 6, the signal controlling system 604 may include an AC signal source 606 configured for applying the electrical signal to the electrical probe 603 and a data acquisition module 607 configured for acquiring the electrical response corresponding to the electrical signal from the electrical probe 603. The AC signal source 606 may be configured to apply a voltage of, for example, about 40 mV to the electrical probe 603. Accordingly, the applied voltage may cause a frequency that ranges from about 100 Hz to about 100 KHz.

Figure 13:
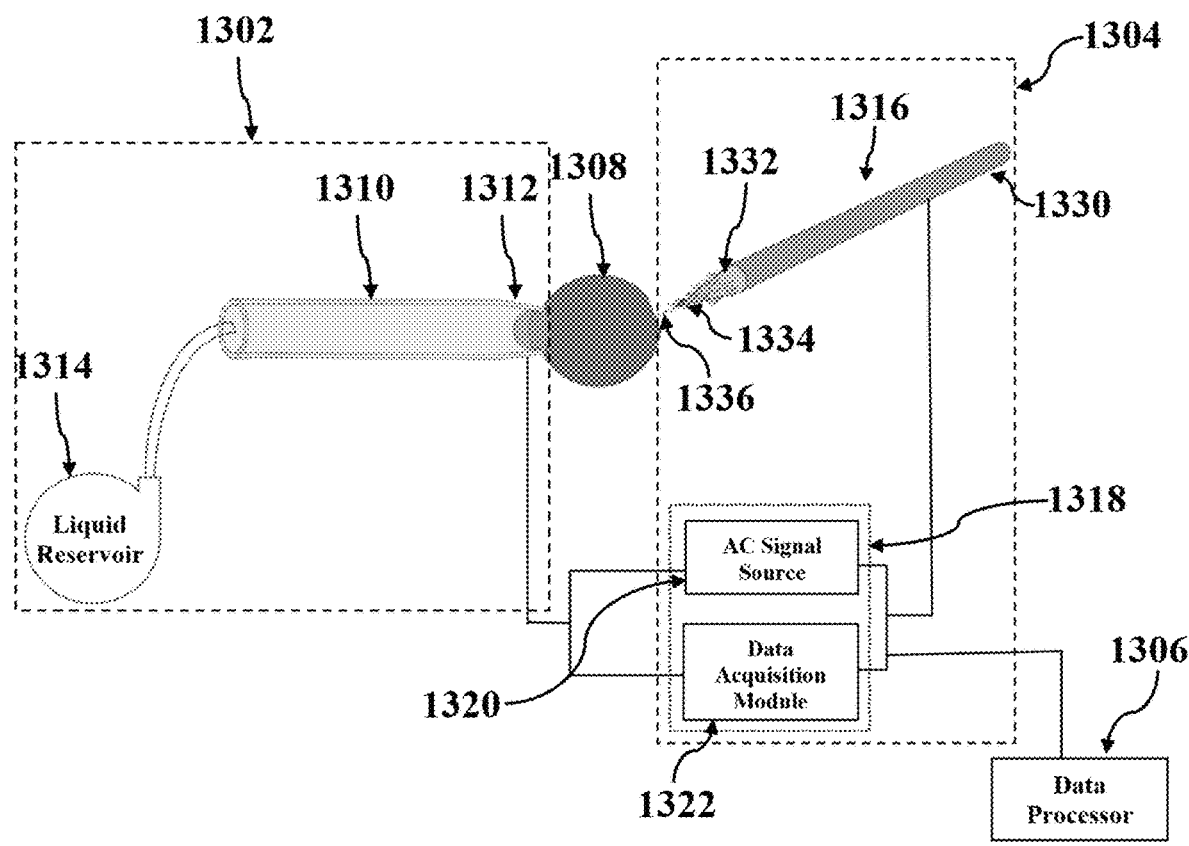
FIG. 13 illustrates a schematic view of an exemplary electromechanical system for detecting cancerous state of a single cell, consistent with one or more exemplary embodiments of the present disclosure.

FIG. 13 shows another exemplary schematic view of electromechanical system 1300 for detecting cancerous state of a single cell, consistent with one or more exemplary embodiments of the present disclosure. Exemplary electromechanical system 1300 may include aspirating mechanism 1302, electrical measurement mechanism 1304, and processing mechanism 1306. In an exemplary implementation, aspirating mechanism 1302 may be configured to extract exemplary single cell 1308 from a suspension of a plurality of suspended biological cells, hold extracted single cell 1308, and apply a mechanical aspiration to the held single cell 1308 by applying a suction force to held single cell 1308. In an exemplary implementation, electrical measurement mechanism 1304 may be configured to apply a set of electrical signals to single cell 1308 before and after applying the mechanical aspiration, measure a first set of electrical responses from held single cell 1308 corresponding to the applied set of electrical signals before the mechanical aspiration, and measure a second set of electrical responses from the mechanically aspirated single cell 1308 respective to the applied set of electrical signals. In an exemplary implementation, processing mechanism 1306 may include data processor 1306, which may be configured to detect cancerous state of single cell 1308 based on a difference between the first set of electrical responses and the second set of electrical responses.

In an exemplary embodiment, single cell 1308 may refer to a biological cell. In an exemplary embodiment, single cell 1308 may refer to a biological cell with elastic cell membrane. In an exemplary embodiment, single cell 1308 may refer to at least one of an epithelial cell, an endothelial cell, a mesenchymal cell, and combinations thereof. In an exemplary embodiment, single cell 1308 may refer to a single cell of a biological sample, where the biological sample may be acquired from an animal or a human body. In an exemplary embodiment, single cell 1308 may refer to a biological cell in a suspension of a plurality of suspended biological cells. In an exemplary embodiment, the biological cells may include a plurality of cells with elastic cell membranes. In an exemplary embodiment, the biological cells may include at least one of epithelial cells, endothelial cells, mesenchymal cells, and combinations thereof.

In an exemplary implementation, the set of electrical signals may include a set of electrical voltages of about 40 mV that may be applied at a set of frequency values in a frequency range between about 100 Hz and about 100 KHz. In an exemplary implementation, each of the first set of electrical responses and the second set of electrical responses may include a set of at least one of electrical impedance values, electrical phase values, and combinations thereof.

In an exemplary implementation, aspirating mechanism 1302 may include an electrically activated micropipette 1310 and liquid reservoir 1314 that may be connected to electrically activated micropipette 1310. In an exemplary implementation, electrically activated micropipette 1310 may be configured to extract single cell 1308 from the suspension of the plurality of suspended biological cells, hold the extracted single cell 1308, and act as an electrical ground potential for electrical measurement mechanism 1304.

In an exemplary embodiment, electrically activated micropipette 1310 may include nozzle 1312 at a first end (not illustrated) of electrically activated micropipette 1310. In an exemplary implementation, nozzle 1312 may be configured to transfer the mechanical aspiration to the held single cell 1308. In an exemplary embodiment, nozzle 1312 may have an inner diameter of about 5 μm.

In an exemplary embodiment, electrically activated micropipette 1310 may include a micropipette and an electrical conductive layer coated on an outer surface of nozzle 1312. In an exemplary embodiment, the electrical conductive layer may include at least one of gold (Au), titanium (Ti), platinum (Pt), and combinations thereof. In an exemplary embodiment, the electrical conductive layer may include a gold layer regarding a low electrical resistivity of gold. In an exemplary embodiment, the electrical conductive layer may include a gold layer with a thickness of about 10 nm or less that may be coated on nozzle 1312 utilizing a sputtering process.

In an exemplary implementation, the electrical conductive layer may be configured to form an electrical connection between aspirating mechanism 1302 and electrical measurement mechanism 1304 that may be required to transmit electricity through an electrical conductive path along a closed electrical circuit between aspirating mechanism 1302 and electrical measurement mechanism 1304. In an exemplary embodiment, the closed electrical circuit may include aspirating mechanism 1302 with electrical conductive layer on nozzle 1312, single cell 1308 with electrical conductive membrane, and electrical measurement mechanism 1304 with electrical conductive elements/connections. In such implementation, electrically activated micropipette 1310 may be configured to function as the electrical ground potential relative to the held single cell 1308 for electrical measurement mechanism 1304. Therefore, electromechanical system 1300 may provide a real-time electrical measurement from the held single cell 1308 during the mechanical aspiration in which a closed electrical circuit may be applied between electrical measurement mechanism 1304 and electrically activated micropipette 1310.

In an exemplary embodiment, the micropipette may be made of at least one of glass, quartz, plastic, and combinations thereof. In an exemplary embodiment, the micropipette may be made of a plastic material with mechanical characteristics (or mechanical coefficients) similar to mechanical characteristics (or mechanical coefficients) of quartz.

In an exemplary embodiment, liquid reservoir 1314 may be connected to a second end (not illustrated) of electrically activated micropipette 1310. In an exemplary embodiment, liquid reservoir 1314 may be configured to function as a pressure source for the mechanical aspiration. In other words, liquid reservoir 1314 may provide the pressure needed for mechanical aspiration in exemplary embodiments.

In an exemplary implementation, aspirating mechanism 1302 may be configured to apply a mechanical aspiration to the held single cell 1308 by adjusting a mechanical pressure that may be applied to electrically activated micropipette 1310 at the second end of electrically activated micropipette 1310. The applied mechanical aspiration to electrically activated micropipette 1310 may be transferred and applied to the held single cell 1308 through nozzle 1312 at the first end of electrically activated micropipette 1310. In an exemplary implementation, the mechanical aspiration of the held single cell 1308 may include applying a positive pressure to the held single cell 1308 that may result in pulling the held single cell 1308 inside itself. In another exemplary implementation, the mechanical aspiration of the held single cell 1308 may include applying a negative pressure (a suction pressure) to the held single cell 1308 that may result in partially stretching the held single cell 1308 into nozzle 1312. In such implementation, a length of the held single cell 1308 may be increased due to the mechanical stretching and the length of the held single cell 1308 may be returned to an initial magnitude that it was at before the mechanical aspiration by returning the applied pressure to zero.

In an exemplary implementation, aspirating mechanism 1302 may be configured to apply a mechanical aspiration to the held single cell 1308 by applying a positive or negative pressure with a magnitude of between 10 Pa and 100 Pa to the held single cell 1308. In an example, aspirating mechanism 1302 may be configured to apply a mechanical aspiration to the held single cell 1308 by applying a positive or negative pressure with a magnitude between 50 Pa and 60 Pa to the held single cell 1308.

In an exemplary implementation, electrically activated glass micropipette 1310 may be assembled on a microinjection microscope (not illustrated). In such implementations, electrically activated glass micropipette 1310 may be held by a first arm of the microinjection microscope; allowing for observation and control of aspirating mechanism 1302. In an exemplary embodiment, observation of aspirating mechanism 1302 may refer to at least one of observation of single cell 1308 utilizing the microinjection microscope, visually monitor a process of extracting single cell 1308 utilizing electrically activated glass micropipette 1310, observation of holding extracted single cell 1308 utilizing electrically activated glass micropipette 1310, and visually monitor a process and magnitude of the mechanical aspiration of the held single cell 1308, and combinations thereof. In an exemplary embodiment, control of aspirating mechanism 1302 may refer to adjust a location of nozzle 1312 to conduct at least one of extraction of single cell 1308, holding the extracted single cell 1308, and applying the mechanical aspiration to the held single cell 1308, and combinations thereof.

In an exemplary implementation, liquid reservoir 1314 may include at least one of a manually movable water reservoir of the microinjection microscope and an automatically movable water reservoir of the microinjection microscope. In an exemplary implementation, a location (height) of liquid reservoir 1314 may be adjusted manually or automatically, for example, utilizing a tuning screw. In an exemplary implementation, liquid reservoir 1314 may be configured to move downward to supply a suction pressure for the mechanical aspiration or move upward to supply a positive pressure for the mechanical aspiration. A magnitude of the applied pressure may be adjusted by upwardly displacing liquid reservoir 1314 and/or downwardly displacing liquid reservoir 1314.

In an exemplary implementation, electrical measurement mechanism 1304 may include electrical probe 1316 and signal controlling system 1318. In an exemplary embodiment, signal controlling system 1318 may be electrically connected to electrical probe 1316 and data processor 1306. In an exemplary implementation, electrical probe 1316 may be configured to connect to the held single cell 1308. In an exemplary implementation, signal controlling system 1318 may be configured to apply an electrical signal to the held single cell 1308 via electrical probe 1316 and acquire an electrical response corresponding to the applied electrical signal from the held single cell 1308 via electrical probe 1316. In an exemplary embodiment, the electrical signal may include an electrical voltage of about 40 mV in a frequency range between about 100 Hz and about 100 KHz. In an exemplary embodiment, the electrical response may include at least one of an electrical impedance of the held single cell 1308, an electrical phase of the held single cell 1308, and combinations thereof.

Figure 14:
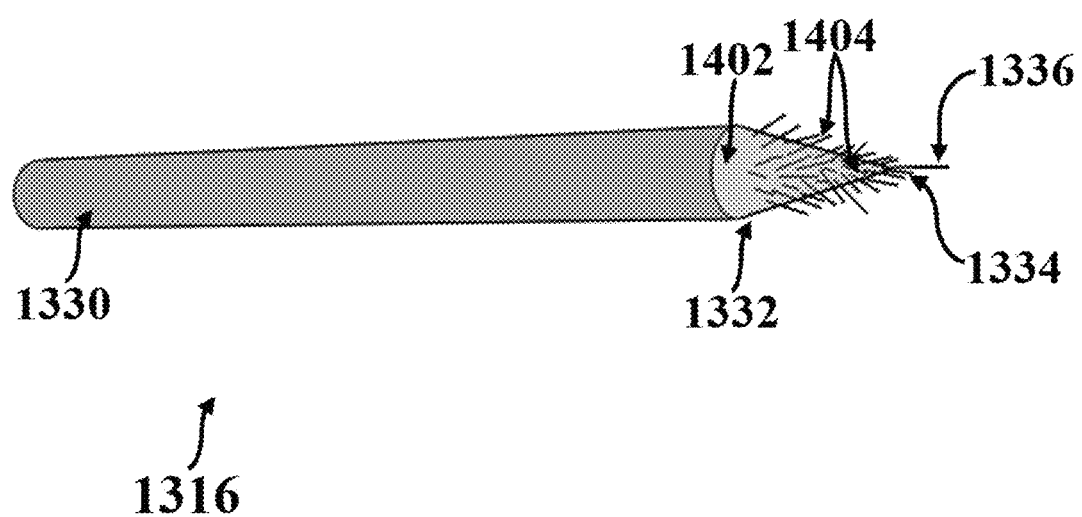
FIG. 14 illustrates a magnified schematic view of an exemplary electrical probe for electrical measurements from a single cell, consistent with one or more exemplary embodiments of the present disclosure.

FIG. 14 shows a magnified schematic view of electrical probe 1316 for electrical measurements from a single cell, consistent with one or more exemplary embodiments of the present disclosure. Referring to FIGS. 13 and 14, electrical probe 1316 may include tungsten microwire 1330, catalyst layer 1402, array of nanotube electrodes 1404, and an electrically conductive layer (not illustrated) that may be coated over each electrode of array of nanotube electrodes 1404.

In an exemplary embodiment, tungsten microwire 1330 may have a sharpened tip section 1332 with a sharp pointed tip 1334. In an exemplary embodiment, tungsten microwire 1330 may include a microwire made of tungsten (W) with a diameter of about 500 µm or less. In an exemplary embodiment, sharp pointed tip 1334 may have a diameter of about 10 µm or less. In an exemplary embodiment, sharp pointed tip 1334 may have a diameter of about 200 nm or less.

In an exemplary embodiment, catalyst layer 1402 may be formed (i.e. deposited) on sharpened tip section 1332 of tungsten microwire 1330. In an exemplary embodiment, catalyst layer 1402 may include a catalyst for growth of array of nanotube electrodes 1404 thereon. In an exemplary embodiment, catalyst layer 1402 may include a catalyst bilayer that may include a nickel layer over a gold layer. In an exemplary embodiment, catalyst layer 1402 may include the nickel layer with a thickness in a range between about 10 nm and about 40 nm over the gold layer with a thickness in a range between about 1 nm and about 4 nm.

In an exemplary embodiment, array of nanotube electrodes 1404 may include array of nanotube electrodes 1404 that may be vertically aligned on catalyst layer 1402. In an exemplary embodiment, array of nanotube electrodes 1404 may include a plurality of doped silicon nanotubes (SiNTs) that may include an array of doped SiNTs with enhanced electrical conductivity. In an exemplary embodiment, the array of doped SiNTs may include a plurality of doped SiNTs with phosphorus.

In an exemplary embodiment, array of nanotube electrodes 1404 may include a long free-end silicon nanotube 1336 that may be located on sharp pointed tip 1334. In an exemplary embodiment, long free-end silicon nanotube 1336 may be longer than remaining SiNTs of the plurality of doped SiNTs. In an exemplary embodiment, long free-end silicon nanotube 1336 may be configured to connect with and penetrate into the held single cell 1308. In an exemplary embodiment, long free-end silicon nanotube 1336 may be configured to penetrate into the held single cell 1308 with a superficial and negligibly invasive cell penetration, which may ensure high electrical sensitivity of electrical probe 1316.

In an exemplary embodiment, electrically conductive layer (not illustrated), which may be coated over array of nanotube electrodes 1404, may include a gold layer that may be coated over the plurality of doped SiNTs. In an exemplary embodiment, the gold layer may be configured to further enhance the electrical conductivity of the plurality of doped SiNTs. In an exemplary embodiment, the gold layer may include a gold layer with a thickness of about 10 nm or less that may be coated over the plurality of doped SiNTs utilizing a sputtering process. In an exemplary embodiment, the gold layer may include a gold layer with a thickness of about 5 nm or less.

Referring to FIG. 13, signal controlling system 1318 may include AC signal source 1320 and data acquisition module 1322. In an exemplary embodiment, AC signal source 1320 may be configured to apply the electrical signal to electrical probe 1316. In an exemplary embodiment, data acquisition module 1322 may be configured to acquire the electrical response corresponding to the applied electrical signal from electrical probe 1316 and send the electrical response to data processor 1306. In an exemplary embodiment, AC signal source 1320 may be configured to apply a voltage of about 40 mV in a frequency range between about 100 Hz and about 100 KHz to electrical probe 1316.

In an exemplary embodiment, electrical probe 1316 may be assembled (or installed) on a microinjection microscope. In an exemplary embodiment, both electrical probe 1316 and electrically activated glass micropipette 1310 may be assembled on the microinjection microscope. In such embodiments, electrically activated glass micropipette 1310 may be held by a first arm of the microinjection microscope and electrical probe 1316 may be held by a second arm of the microinjection microscope; allowing for observing and controlling aspirating mechanism 1302 of single cell 1308 and penetrating long free-end silicon nanotube 1336 of electrical probe 1316 into single cell 1308.

In an exemplary embodiment, electrical probe 1316 and electrically activated glass micropipette 1310 may be connected to signal controlling system 1318 utilizing coaxial wires that may reduce electrical noises. In an exemplary embodiment, electrical probe 1316 and electrically activated glass micropipette 1310 may be placed apart from each other with a distance between about 5 μm and 10 μm. In an exemplary embodiment, electrical probe 1316 and electrically activated glass micropipette 1310 may be placed apart from each other with a distance of about 7 μm.

Furthermore, data processor 1306 may be configured to receive the first set of electrical responses and the second set of electrical responses from electrical measurement mechanism 1304 and calculate the difference between the first set of electrical responses and the second set of electrical responses by calculating a set of difference values between each two respective values of the first set of electrical responses and the second set of electrical responses. In an exemplary embodiment, data processor 1306 may be further configured to detect single cell 1308 to be cancerous if the calculated difference between the first set of electrical responses and the second set of electrical responses is less than a threshold value. In an exemplary embodiment, data processor 1306 may be further configured to detect single cell 1308 to be cancerous if the calculated difference between the first set of electrical responses and the second set of electrical responses is negligible or near zero.

In an exemplary implementation, data processor 1306 may be configured to detect a cancerous state for single cell 1308 if the calculated difference between the first set of electrical responses and the second set of electrical responses is less than about 30 percent relative to the first set of electrical responses. In another exemplary implementation, data processor 1306 may be further configured to detect a healthy state for single cell 1308 if the calculated difference between the first set of electrical responses and the second set of electrical responses is significant or more than about 30 percent relative to the first set of electrical responses.

In an exemplary implementation, data processor 1306 may be configured to detect the cancerous state for single cell 1308 if the calculated difference between the first set of electrical responses and the second set of electrical responses is less than about 5 percent based on the first set of electrical responses. In another exemplary implementation, data processor 1306 may be further configured to detect the healthy state for single cell 1308 if the calculated difference between the first set of electrical responses and the second set of electrical responses is significant or more than about 5 percent based on the first set of electrical responses.

In an exemplary implementation, the second set of electrical responses may include marked changes relative to the first set of electrical responses due to the mechanical aspiration of the held single cell 1308 for a healthy single cell 1308. In contrast, the second set of electrical responses may include no changes or negligible changes relative to the first set of electrical responses after the mechanical aspiration of the held single cell 1308 for a cancerous single cell 1308.

In an exemplary embodiment, the set of difference values between each two respective values of the first set of electrical responses and the second set of electrical responses may be calculated by following equation:

$$d_i(\%) = \frac{|r_{2i} - r_{1i}|}{r_{1i}} \times 100 \quad \text{Equation (1)}$$

Where, $d_i$ refers to $i^{th}$ difference value of the set of difference values, $r_{2i}$ refers to $i^{th}$ electrical response of the second set of electrical responses, and $r_{1i}$ refers to $i^{th}$ electrical response of the first set of electrical responses. In an exemplary embodiment, single cell 1308 may be detected to be cancerous if all calculated $d_i$s are less than a threshold value. In an exemplary embodiment, single cell 1308 may be detected to be cancerous if all calculated $d_i$s are less than about 30%. In an exemplary embodiment, single cell 1308 may be detected to be cancerous if all calculated $d_i$s are less than about 5%. In an exemplary embodiment, single cell 1308 may be detected to be cancerous if all calculated $d_i$s are near zero.

In another exemplary implementation, data processor 1306 may be further configured to communicate detect cancerous state of single cell 1308 by sending an alarm or sending a message to an expert who may utilize data processor 1306.

Figure 15:
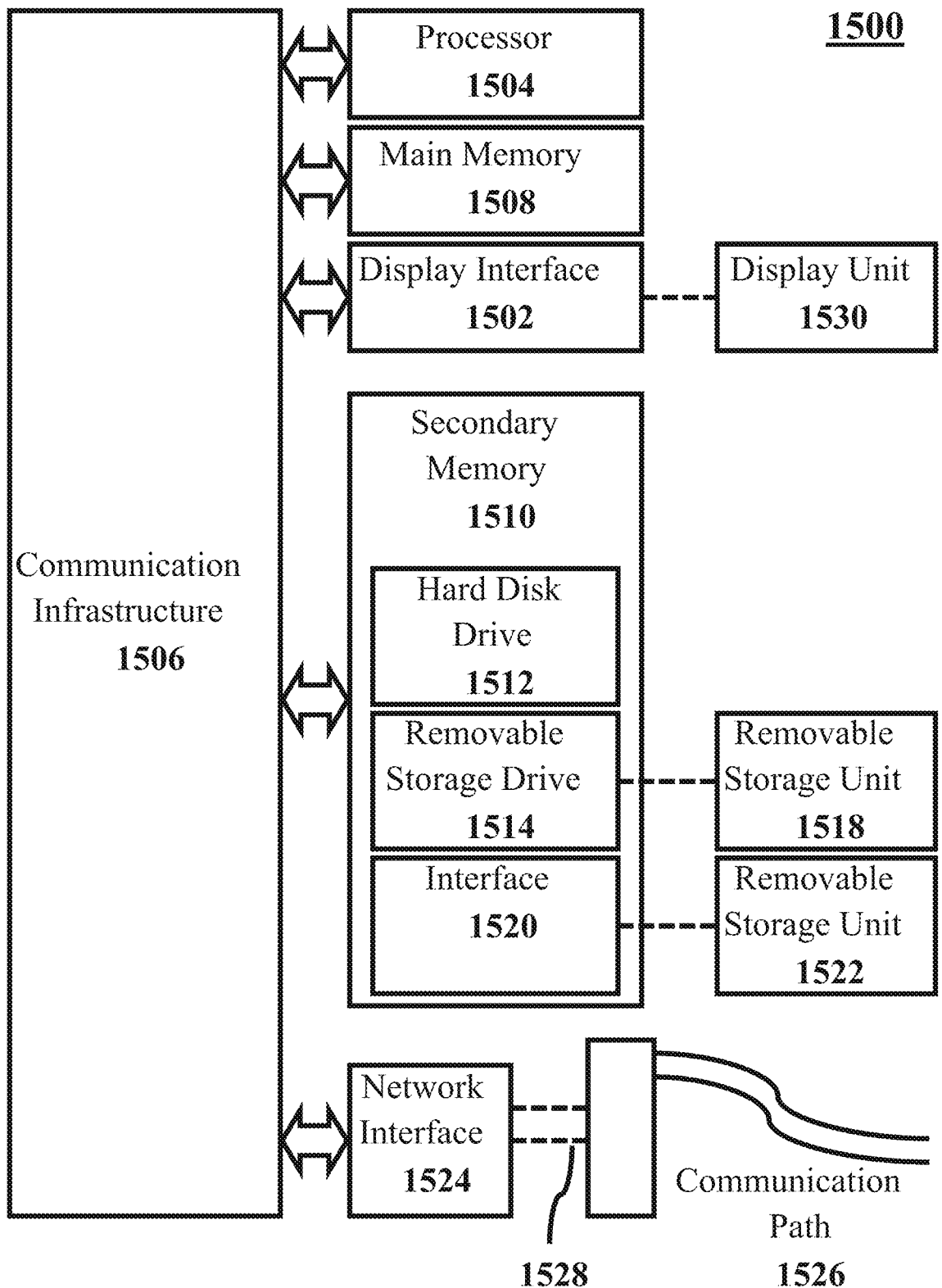
FIG. 15 illustrates an example computer system in which an embodiment of the present disclosure, or portions thereof, may be implemented as computer-readable code, consistent with one or more exemplary embodiments of the present disclosure.

FIG. 15 shows an example computer system 1500 in which an embodiment of the present disclosure, or portions thereof, may be implemented as computer-readable code, consistent with one or more exemplary embodiments of the present disclosure. For example, data processor 1306 may include computer system 1500 with hardware, software, firmware, tangible computer readable media having instructions stored thereon, or a combination thereof and may be configured to have one or more computer systems or other processing systems. Hardware, software, or any combination of such may embody any of the modules and components in FIG. 13. In an exemplary implementation, exemplary computer system 1500 may be utilized to detect cancerous state of single cell 1308 based on the difference between the first set of electrical responses and the second set of electrical responses.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the present disclosure is described in terms of this example computer system 1500 that may function as data processor 1306. After reading this description, it will become apparent to a person skilled in the relevant art how to implement detection of cancerous state of single cell 1308 using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 1504 may be a special purpose or a general-purpose processor device. As will be appreciated by persons skilled in the relevant art, processor device 1504 may also be a single processor in a multi-core/multiprocessor system, such system operating alone, or in a cluster of computing devices operating in a cluster or server farm. Processor device 1504 may be connected to a communication infrastructure 1506, for example, a bus, message queue, network, or multi-core message-passing scheme.

In an exemplary embodiment, computer system 1500 may include a display interface 1502, for example a video connector, to transfer data to a display unit 1530, for example, a monitor. Computer system 1500 may also include a main memory 1508, for example, random access memory (RAM), and may also include a secondary memory 1510. Secondary memory 1510 may include, for example, a hard disk drive 1512, and a removable storage drive 1514. Removable storage drive 1514 may include a floppy disk drive, a magnetic tape drive, an optical disk drive, a flash memory, or the like. Removable storage drive 1514 may read from and/or write to a removable storage unit 1518 in a well-known manner. Removable storage unit 1518 may include a floppy disk, a magnetic tape, an optical disk, etc., which may be read by and written to by removable storage drive 1514. As will be appreciated by persons skilled in the relevant art, removable storage unit 1518 may include a computer usable storage medium having stored therein computer software and/or data.

In alternative implementations, secondary memory 1510 may include other similar means for allowing computer programs or other instructions to be loaded into computer system 1500. Such means may include, for example, a removable storage unit 1522 and an interface 1520. Examples of such means may include a program cartridge and cartridge interface (such as that found in video game devices), a removable memory chip (such as an EPROM, or PROM) and associated socket, and other removable storage units 1522 and interfaces 1520 which allow software and data to be transferred from removable storage unit 1522 to computer system 1500.

Computer system 1500 may also include a communications interface 1524. Communications interface 1524 allows software and data to be transferred between computer system 1500 and external devices. Communications interface 1524 may include a modem, a network interface (such as an Ethernet card), a communications port, a PCMCIA slot and card, or the like. Software and data transferred via communications interface 1524 may be in the form of signals, which may be electronic, electromagnetic, optical, or other signals capable of being received by communications interface 1524. These signals may be provided to communications interface 1524 via a communications path 1526. Communications path 1526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 1518, removable storage unit 1522, and a hard disk installed in hard disk drive 1512. Computer program medium and computer usable medium may also refer to memories, such as main memory 1508 and secondary memory 1510, which may be memory semiconductors (e.g. DRAMs, etc.).

Computer programs (also called computer control logic) are stored in main memory 1508 and/or secondary memory 1510. Computer programs may also be received via communications interface 1524. Such computer programs, when executed, enable computer system 1500 to implement different embodiments of the present disclosure as discussed herein. In particular, the computer programs, when executed, enable processor device 1504 to implement the processes of the present disclosure, such as the operations which may be conducted by data processor 1306 of electromechanical system 1300 shown in FIG. 13, discussed above. Accordingly, such computer programs represent controllers of computer system 1500. Where an exemplary embodiment of mechanisms of electromechanical system 1300 is implemented using software, the software may be stored in a computer program product and loaded into computer system 1500 using removable storage drive 1514, interface 1520, and hard disk drive 1512, or communications interface 1524.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

Example 1: Fabricating a SiNT/W Probe

Figure 7A:
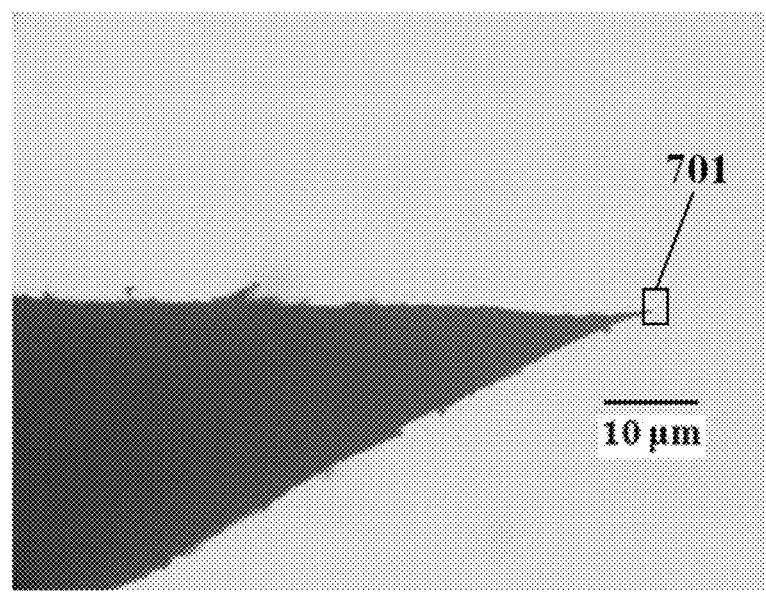
FIG. 7A illustrates an optical image of an example of a sharpened tip of a tungsten (W) needle, consistent with one or more exemplary embodiments of the present disclosure.
Figure 7B:
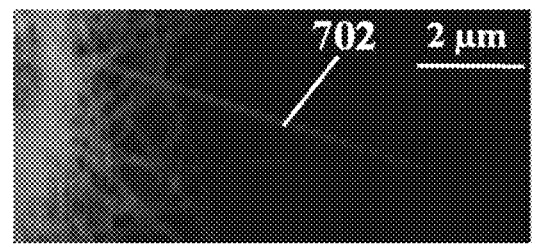
FIG. 7B illustrates a field emission scanning electron microscope (FESEM) micrograph of an example of grown array of SiNTs over the sharpened tip of a W needle, consistent with one or more exemplary embodiments of the present disclosure.
Figure 7C:
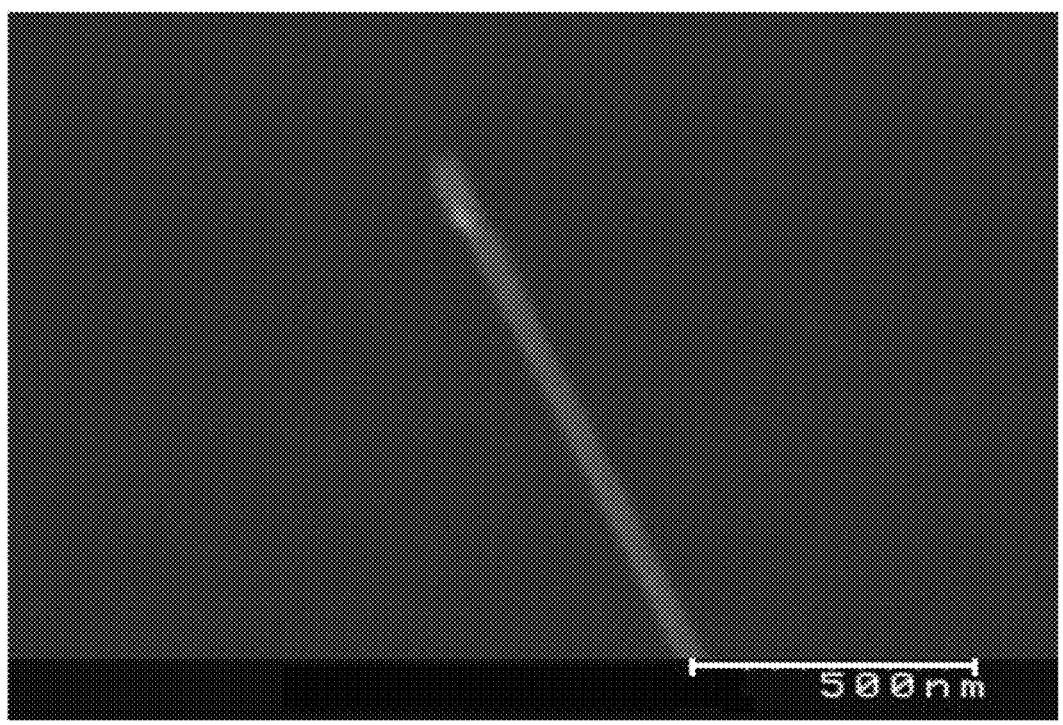
FIG. 7C illustrates a field emission scanning electron microscope (FESEM) micrograph of an example of a single long free end silicon nanotube (SiNT) among an array of SiNTs grown over a sharpened tip of a W needle, consistent with one or more exemplary embodiments of the present disclosure.

In this exemplary scenario, a tungsten (W) needle as a support for a SiNT/W probe is made from an initial W microwire with a diameter of about 500 using an electrochemical etching process. An optical image of an example sharpened tip of a W needle is shown in FIG. 7A, representing the formed tip at one end of the needle with a diameter of about 200 nm. The W needle was washed and cleaned with a solution of acetone and Buffer HF. Subsequently, the cleaned needle was held in an electron beam coating system to deposit a bilayer catalyst of Nickel-Gold (Ni—Au) on the sharp tip of the cleaned W needle. During the deposition process, the needle was placed in a position in which, the top portion of the needle was located in front of the target plume. The deposition was begun at a base pressure of about $10^{-6}$ Torr. A thin layer of gold, with a thickness of about 2 nm was coated on the tip of the probe. Subsequently, another layer of nickel with a thickness of about 20 nm was coated over the gold layer. In a next step, the growth of SiNTs on the catalyst bilayer was achieved via placing the W needle coated with the Ni—Au catalyst over the tip in a LPCVD chamber. The SiNTs were grown over the catalyst bilayer by the assistance of $H_2$ and $SiH_4$ gases at a base pressure of about 1 mTorr and at a temperature of about 450° C. to form the SiNT/W needle. A magnified zone of FIG. 7A represented by 701 is shown in FIG. 7B. This figure illustrates a field emission scanning electron microscope (FESEM) image of an example grown array of SiNTs over the sharpened tip of a W needle. Then, the SiNT/W needle was transferred into a phosphorous doping furnace and held at a temperature of about 700° C. for about 10 minutes to enhance the conductivity of the nanotubes by the diffusion of phosphorous dopants atoms. Finally, a gold layer with a thickness of about 5 nm was coated on top of the nanotubes with the assistance of a sputtering system to form the SiNT/W probe. FIG. 7C illustrates a field emission scanning electron microscope (FESEM) micrograph of an example of a single silicon long free end nanotube (SiNT) 702 of FIG. 7B among the array of SiNTs over the sharpened tip of a W needle, the most appropriate SiNT among the SiNTs array for further superficial and negligibly invasive cell connection and penetration electrical measurement purposes causing the least electrical noises. This figure also shows a diameter of about 70 nm for the formed SiNT on the probe tip.

Example 2: Investigation of the Electrical Sensitivity

In this example, the basic electrical sensitivity of the disclosed system may be characterized by entering and placing a SiNT/W probe and an electrically activated glass micropipette of the system pursuant to the present disclosure in an ionic cellular media solution containing a biological cell suspension, followed by comparing the sensitivity before and after connecting the SiNT/W probe to the cell grasped by the micropipette, and finally by scaling under a dry atmosphere.

Figure 8A:
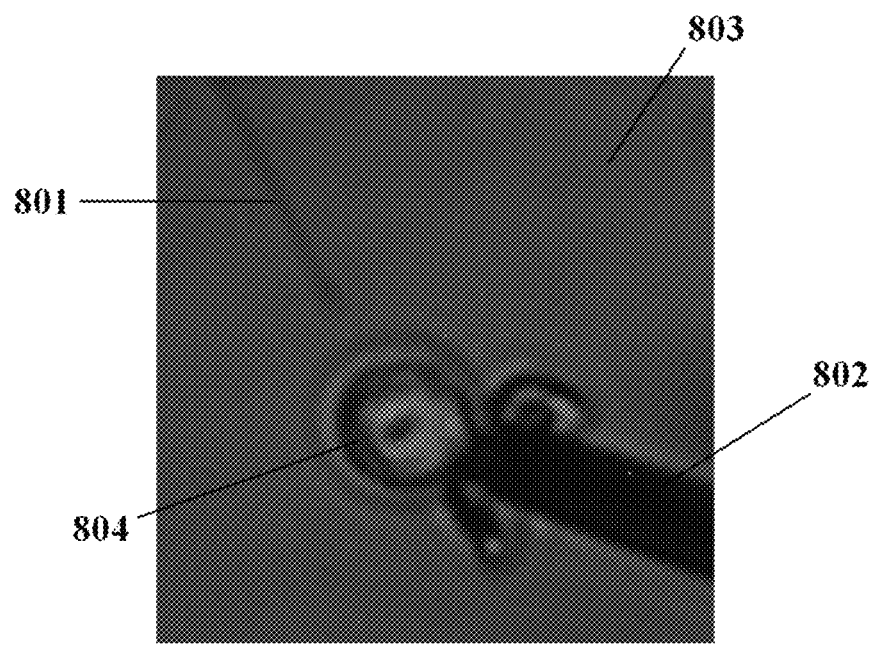
FIG. 8A illustrates an optical image of an example of a single biological cell held by assistance of an electrically activated micropipette and a long free end SiNT of a SiNT/W probe placed in a cellular media solution, consistent with one or more exemplary embodiments of the present disclosure.
Figure 8B:
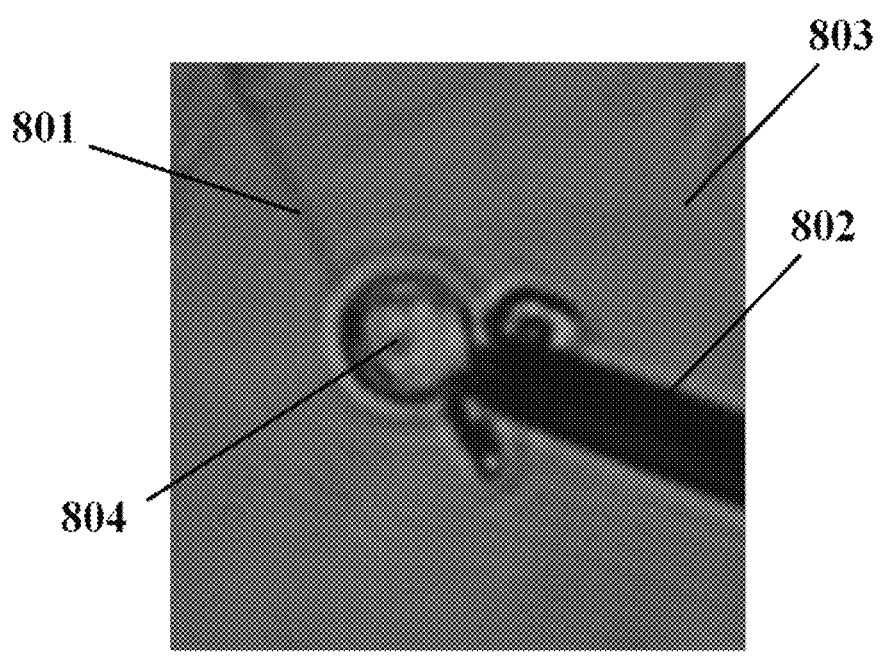
FIG. 8B illustrates an optical image of an example single biological cell held and aspirated by assistance of an electrically activated micropipette and connected to a long free end SiNT of a SiNT/W probe, consistent with one or more exemplary embodiments of the present disclosure.
Figure 8C:
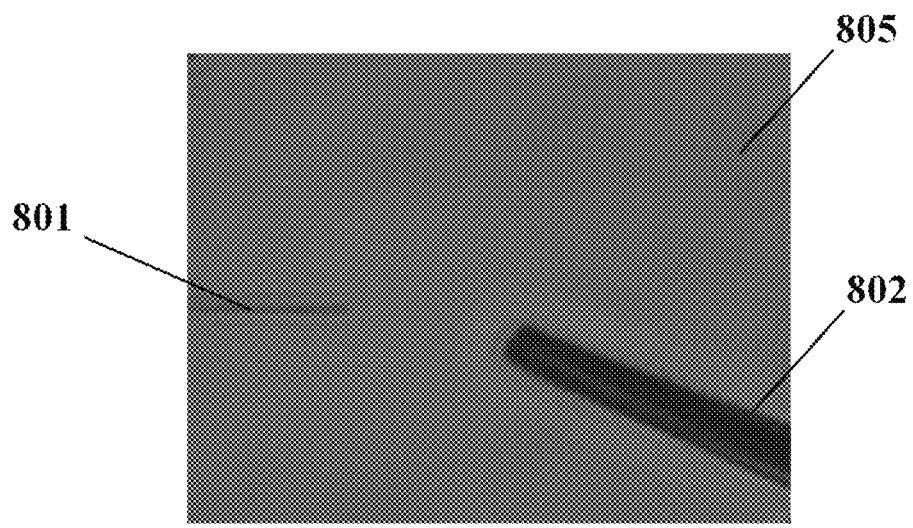
FIG. 8C illustrates an optical image of an example electrically activated micropipette and a long free end SiNT of a SiNT/W probe placed in the air atmosphere, consistent with one or more exemplary embodiments of the present disclosure.

FIGS. 8A-8C show optical images of three situations configured for measurement of the electrical response before (FIG. 8A) and after (FIG. 8B) the connection of the SiNT/W probe to the cell within a cellular media solution and finally in a dry ambient atmosphere (FIG. 8C), consistent with one or more exemplary embodiments of the present disclosure.

Referring to FIG. 8A, an optical image of a long free end SiNT 801 of a SiNT/W probe and an electrically activated micropipette 802 placed in a cellular media solution 803 is illustrated. A single biological cell 804 was selected and held within the cellular media solution 803 by assistance of the electrically activated micropipette 802, while the probe may be placed over the cell without any connections to the cell. FIG. 8B shows a second situation similar to FIG. 8A, while the long free-end SiNT 801 connected and penetrated the single biological cell 804 aspirated by the electrically activated micropipette 802. Subsequently, FIG. 8C shows a third exemplary situation, in which the long free-end SiNT 801 of a SiNT/W probe and the electrically activated micropipette 802 are placed in a dry air atmosphere 805.

Figure 9A:
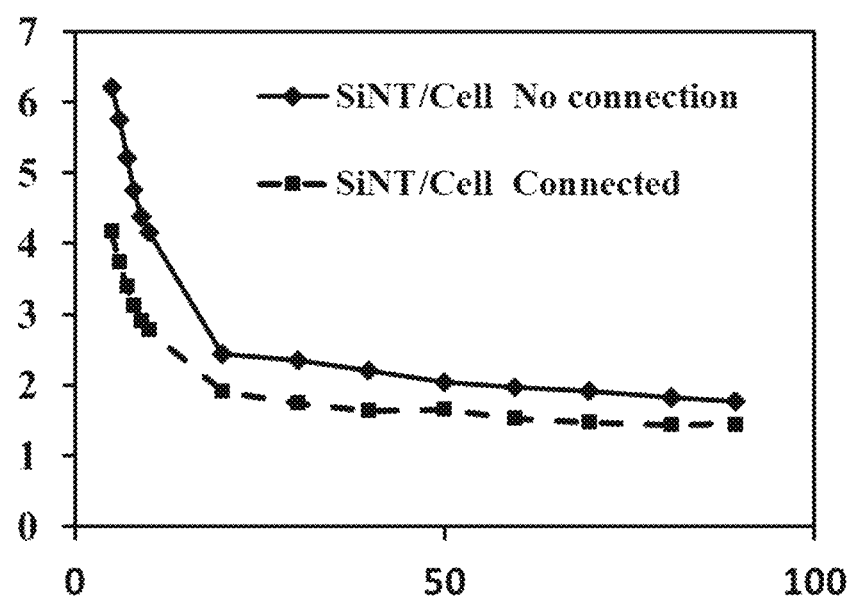
FIG. 9A is an electrical impedance (electrical sensitivity) curve measured in a cellular media solution for a frequency range of about 0 KHz to about 100 KHz in two situations of: SiNT not connected to a single cell (solid line) and SiNT connected to a single cell (dashed line), consistent with one or more exemplary embodiments of the present disclosure.
Figure 9B:
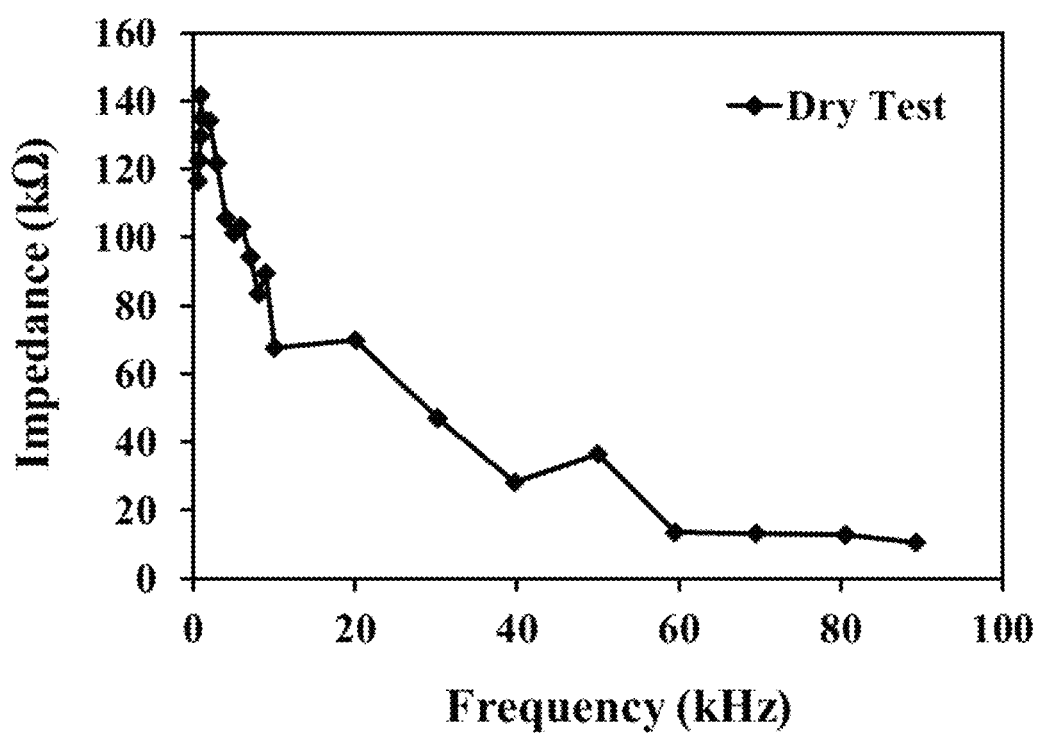
FIG. 9B is an electrical impedance (electrical sensitivity) curve measured in an air atmosphere for a frequency range of about 0 KHz to about 100 KHz, consistent with one or more exemplary embodiments of the present disclosure.

FIGS. 9A and 9B show corresponding electrical impedance (electrical sensitivity) values that are measured in a frequency range of about 0 KHz to about 100 KHz for the three exemplary situations described above and shown in FIGS. 8A-8C, consistent with one or more exemplary embodiments of the present disclosure. Referring to FIG. 9A, representing the impedance values for the first and second situations within the cellular media solution, the impedance curves are obtained for the cases, where the SiNT is not connected to the single cell (designated by the solid line) and where the SiNT is connected to the single cell (designated by the dashed line) are within a similar range of about 1 kΩ to about 7 kΩ, while regarding FIG. 9B, the impedance magnitudes increased significantly to a range of about 0 kΩ to about 140 kΩ when the ambient was changed from a cellular media solution to an air atmosphere in a fixed distance between the SiNT and the micropipette (about 7 μm).

Example 3: Detecting the Cancerous State of a Single Cell

In this example, the electromechanical method and system were used to detect the cancerous state of a single cell. To this end, healthy lung cells (MRC-5) and cancerous lung cells (QU-DB) were utilized. The MRC-5 was derived from a healthy or normal lung tissue and QU-DB was derived from a human lung carcinoma tissue. For cell culturing, cells were maintained in a $CO_2$ incubator (37° C., 5% $CO_2$, 95% air) in a RPMI-1640 medium supplemented with 5% fetal bovine serum, and 1% penicillin/streptomycin. The fresh medium was replaced every day. Prior to each experiment, cells were trypsinized in order to be detached from the substrate and were suspended in the culture medium. To minimize the effect of trypsinization, the procedure was carried out in less than 4 minutes at a temperature of about 20-22° C. Single cells suspended within the prepared suspension were extracted, held and aspirated by an electrically activated glass micropipette having a nozzle with an inner diameter of about 5 Then, the SiNT/W probe was connected to the aspirated cell and an electrical response (impedance magnitude and phase) were measured for different suction forces applied by the micropipette.

Figure 10A:
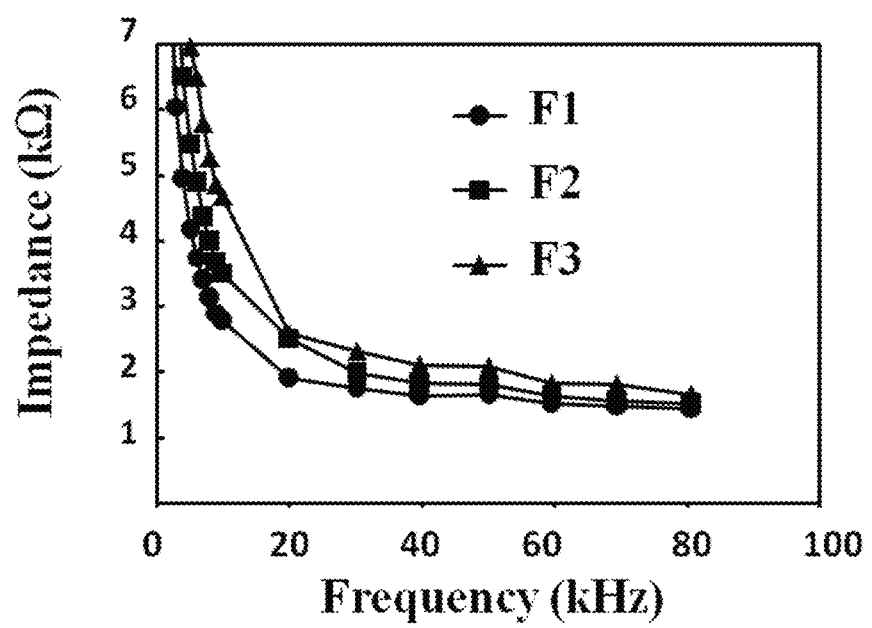
FIG. 10A illustrates a cell impedance versus frequency curve for an example of an aspirated MRC-5 single cell with three different suction amplitudes, consistent with one or more exemplary embodiments of the present disclosure.
Figure 10B:
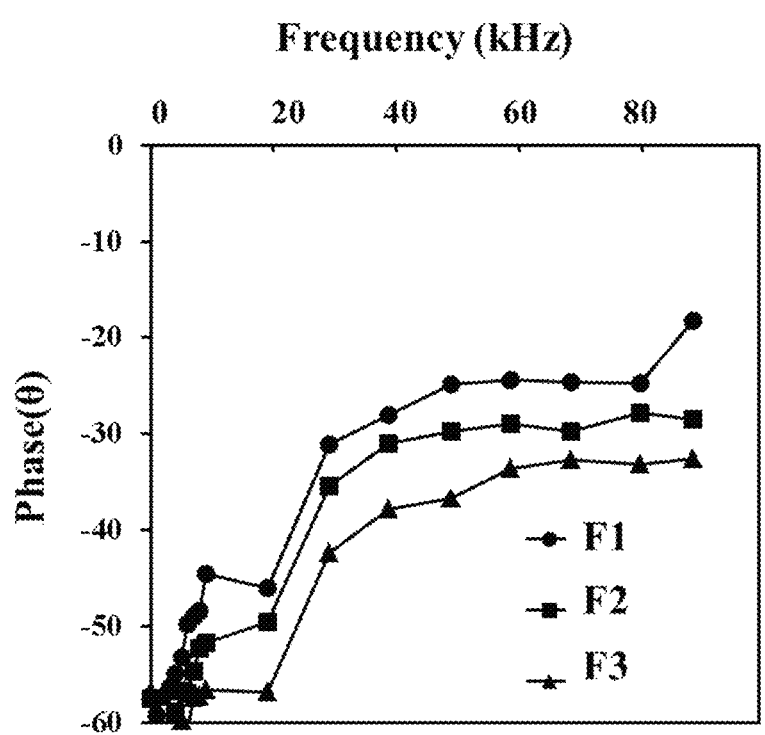
FIG. 10B is a phase response versus frequency curve for an example of an aspirated MRC-5 single cell with three different suction amplitudes, consistent with one or more exemplary embodiments of the present disclosure.
Figure 10C:
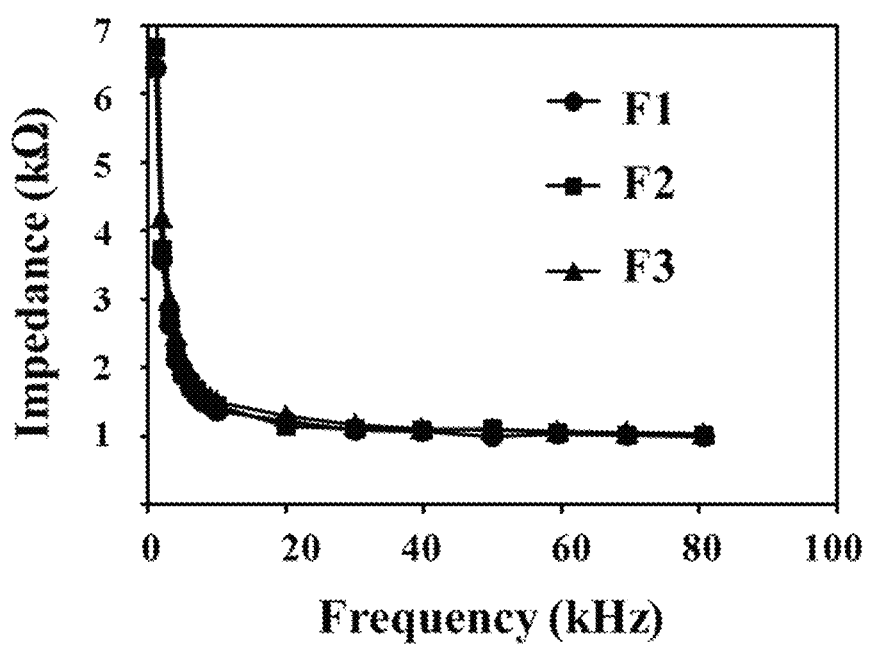
FIG. 10C is a cell impedance versus frequency curve for an example of an aspirated QU-DB single cell with three different suction amplitudes, consistent with one or more exemplary embodiments of the present disclosure.
Figure 10D:
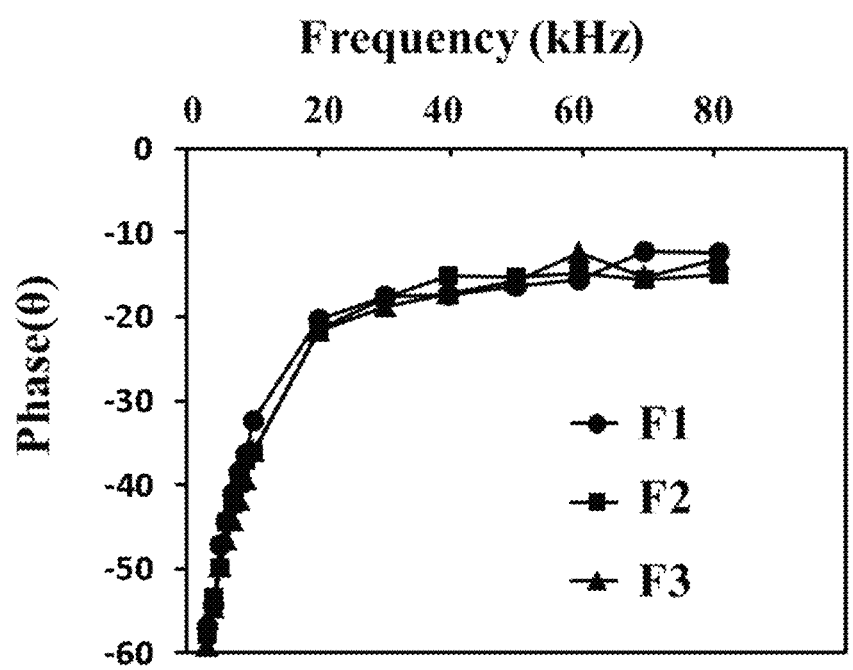
FIG. 10D is a phase response versus frequency curve for an example of an aspirated QU-DB single cell with three different suction amplitudes, consistent with one or more exemplary embodiments of the present disclosure.

FIGS. 10A-10D show the results of the electrical measurements from aspirated MRC-5 and QU-DB cells with various suction forces, consistent with one or more exemplary embodiments of the present disclosure. The representative recorded data in FIGS. 10A and 10B show a clear increase in the cell impedance and phase with increasing mechanical stretch amplitudes from F1 to F3 in healthy cells (MRC-5), whereas no noticeable impedance and phase changes were observed in malignant cells after increasing the aspiration with the same suction forces as shown in FIGS. 10C and 10D.

The suction forces during cell aspiration resulted in different lengths of the cell that flowed into the pipette (Lp) due to the mechanical properties of each individual cell. The Lp value was determined from microscopy images. Table 1 shows the Lp (μm) values and corresponding changes in electrical responses (electrical impedance (kΩ) and phase (θ)) for each single cell that was aspirated by three increasing various suction forces of F1, F2 and F3. The data shows that changes in the electrical parameters initiated from mechanical aspiration in healthy lung cells (MRC-5) were about 10 times higher than those of aspirated cancerous cells (QU-DB). These results suggest that bioelectrical properties of a healthy cell have a strong correlation with its mechanical function.

Furthermore, the effects of cancerous transformation and cell aspiration on actin microfilament distribution on control and stretched MRC-5 and QU-DB cell samples were assessed by inverted confocal microscopy. Prior to imaging, cells were fixed in about 4% formaldehyde for about 15 min and permeabilized in PBS (with the concentration of about 1%) for about 5 min to 10 min at room temperature. Then, all samples were washed and stained with the phalloidin-FITC conjugate (Green) and incubated for about 30 min to 45 min. The cell nuclei were stained with propidium iodide (PI). The Leica Application Suite Advanced Fluorescence (LAS AF) software (Leica Microsystems) was utilized to analyze the confocal microscopy images.

Figure 11A:
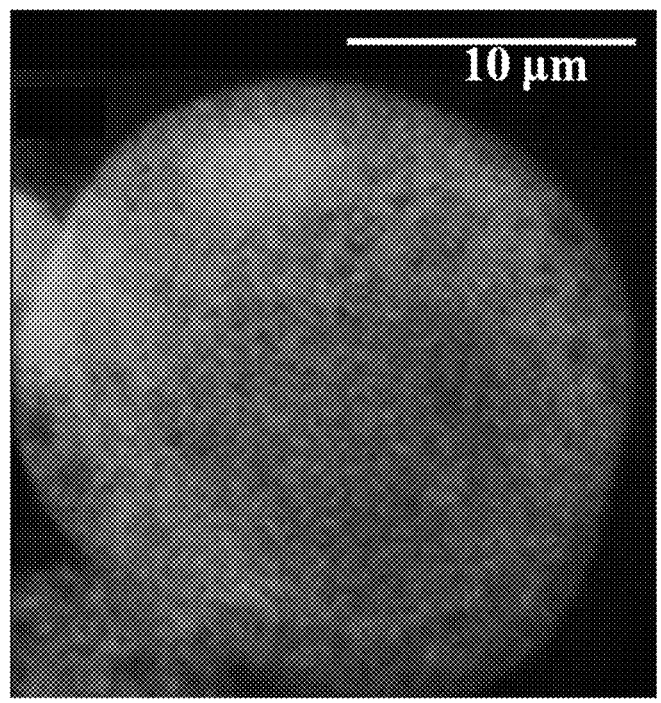
FIG. 11A illustrates a confocal microscope image of an example of a control MRC-5 cell before mechanical aspiration, consistent with one or more exemplary embodiments of the present disclosure.
Figure 11B:
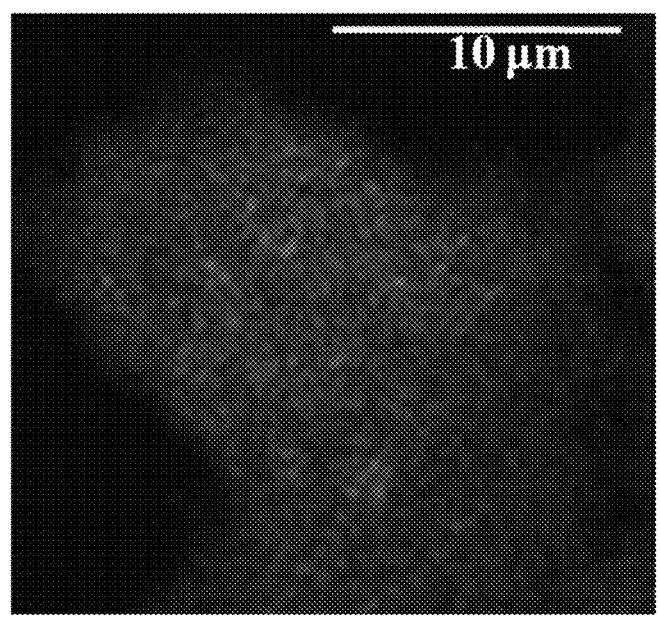
FIG. 11B illustrates a confocal microscope image of an example of a MRC-5 cell after mechanical aspiration, consistent with one or more exemplary embodiments of the present disclosure.
Figure 11C:
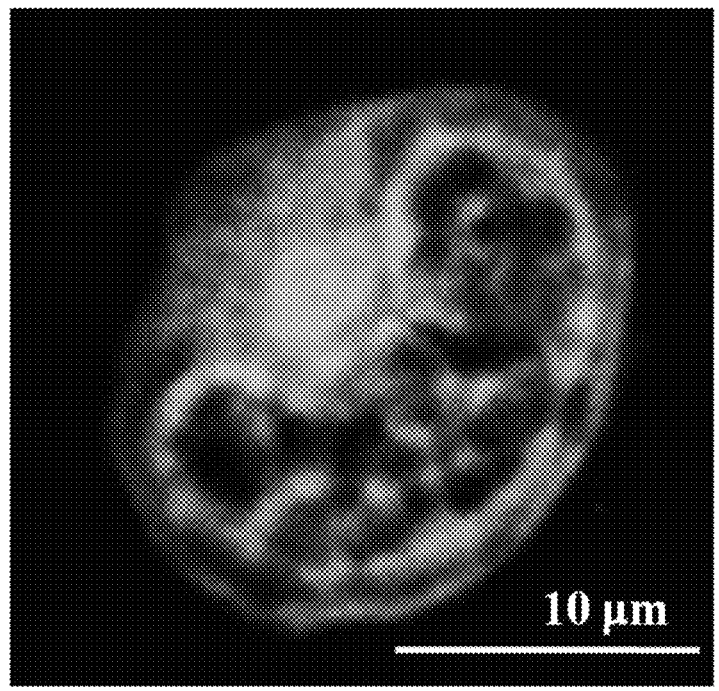
FIG. 11C illustrates a confocal microscope image of an example of a control QU-DB cell before mechanical aspiration, consistent with one or more exemplary embodiments of the present disclosure.
Figure 11D:
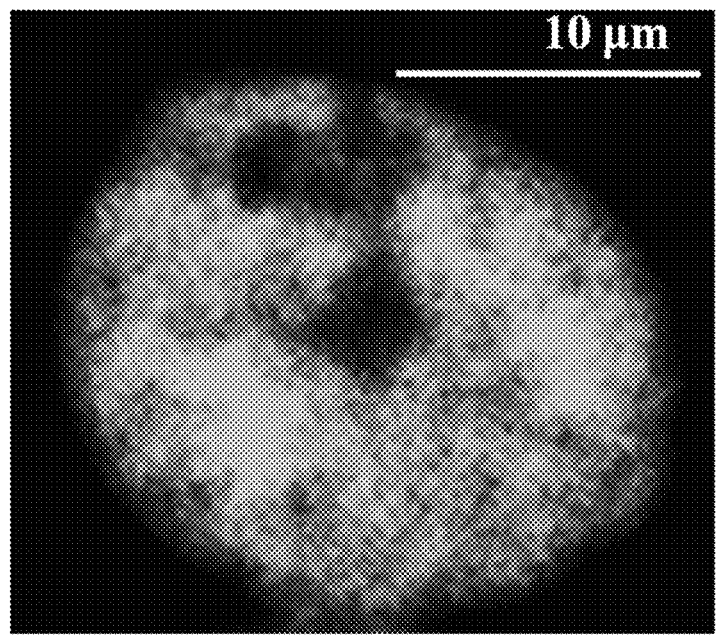
FIG. 11D illustrates a confocal microscope image of an exemplary QU-DB cell after mechanical aspiration, consistent with one or more exemplary embodiments of the present disclosure.

FIG. 11A shows a confocal microscope image of a control MRC-5 cell before aspiration, while a confocal microscope image of an aspirated MRC-5 cell is shown in FIG. 11B. FIGS. 11A and 11B show that the mechanical aspiration results in major alterations in the actin microfilaments for MRC-5 cell. Also, corresponding images are shown in FIGS. 11C and 11D representing confocal microscopy images of a control QU-DB cell before aspiration (FIG. 11C) and after aspiration (FIG. 11D) illustrating less alterations in cell actin microfilaments structure for a QU-DB in comparison with those alterations for MRC-5 cell. It may be concluded that cancerous transformation resulted in the rebundling of actin microfilaments during aspiration mechanism, so the mechanical properties and subsequently electrical properties of a cancerous cell would remain the same before and after cell aspirating. As a result, confocal microscopy showed the crucial role of actin microfilaments in cells that had highly reduced electromechanical behavior after metastatic progression. It showed the distinct differences in actin microfilament configurations between the control samples of healthy and malignant lung cells. The images showed that the actin microfilaments are bundled and remodeled in QU-DB cells during mechanical aspiration, while the actin microfilaments configurations of a healthy MRC-5 cell is significantly changed applying a mechanical aspiration.

Example 4: Detecting Cell Metastasis Progression

In this example, in order to elucidate the effect of metastasis progression of cancer cells on their electromechanical response, some experiments were performed on colon primary (HT-29) and progressive (SW-48) malignant cells. The colon primary or benign cells (HT-29) and colon progressive or metastatic (SW-48) malignant cells were obtained from the National Cell Bank of Iran, Pasteur Institute. Both types of cells were cultured, suspended and their electrical properties were measured before and after mechanical aspiration, identical to the methods and techniques described in connection with example 3.

Figure 12A:
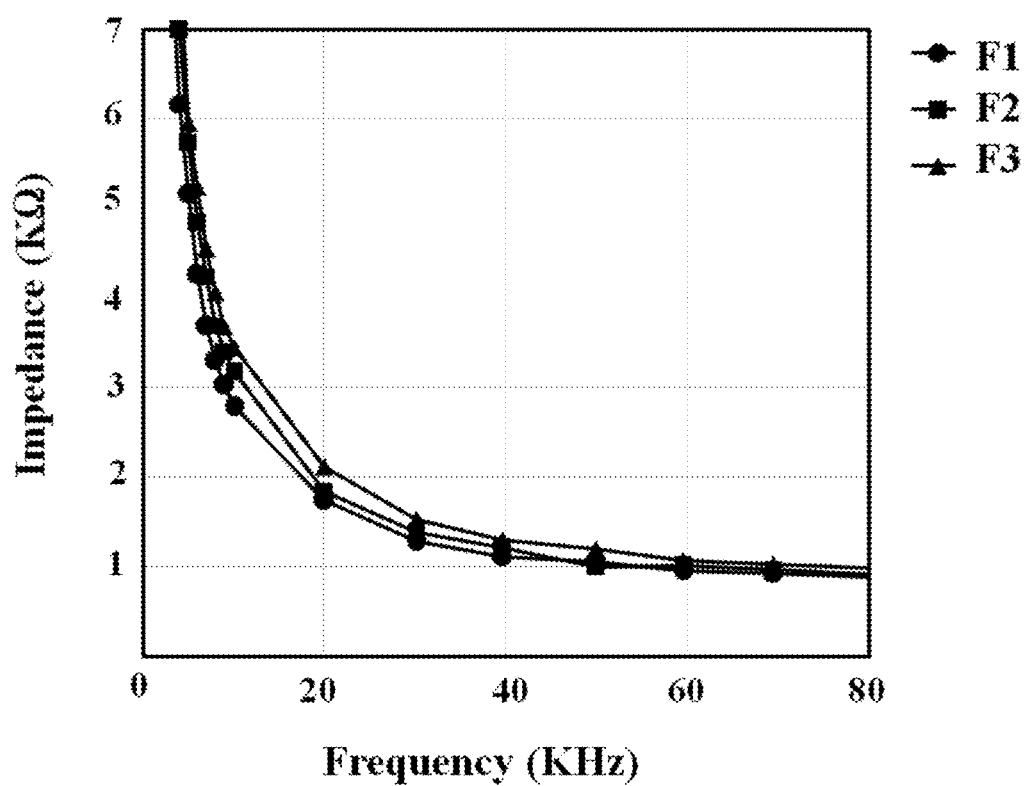
FIG. 12A is a cell impedance versus frequency curve for an exemplary aspirated HT-29 single cell with three different suction amplitudes, consistent with one or more exemplary embodiments of the present disclosure.
Figure 12B:
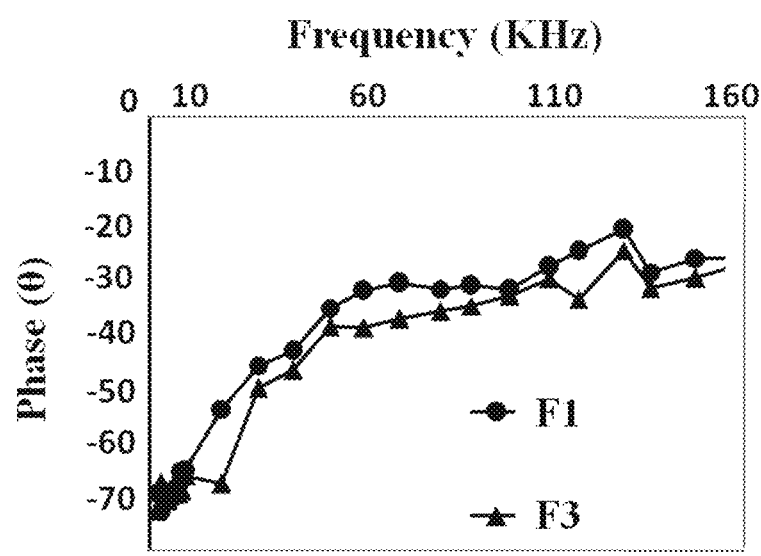
FIG. 12B is a phase response versus frequency curve for an exemplary aspirated HT-29 single cell with two different suction amplitudes, consistent with one or more exemplary embodiments of the present disclosure.
Figure 12C:
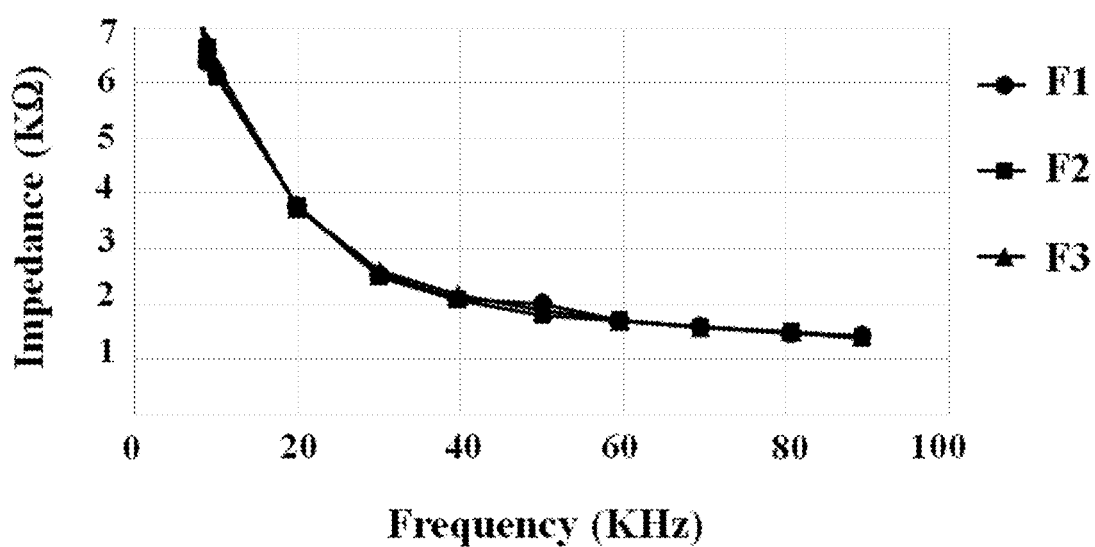
FIG. 12C is a cell impedance versus frequency curve for an exemplary aspirated SW-48 single cell with three different suction amplitudes, consistent with one or more exemplary embodiments of the present disclosure.
Figure 12D:
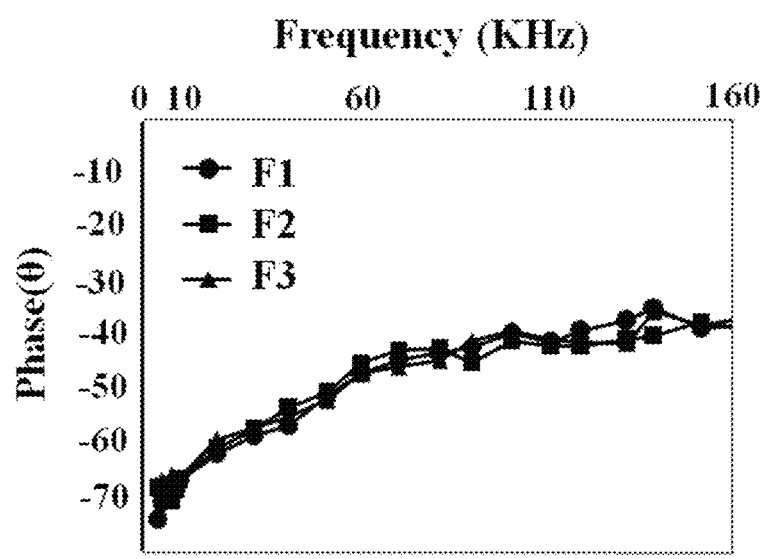
FIG. 12D is a phase response versus frequency curve for an exemplary aspirated SW-48 single cell with three different suction amplitudes, consistent with one or more exemplary embodiments of the present disclosure.

FIGS. 12A-12D show the results of the electrical measurements from aspirated HT-29 and SW-48 cells after applying three various suction forces (F1, F2 and F3) during mechanical aspiration, consistent with one or more exemplary embodiments of the present disclosure. The representative recorded data in FIGS. 12A and 12B show an increase in the cell impedance and phase with increasing mechanical stretch amplitudes from F1 to F3 for HT-29, whereas no noticeable impedance and phase changes were observed for SW-48 after increasing the aspiration with the same suction forces as shown in FIGS. 12C and 12D.

The suction forces during cell aspiration resulted in different lengths of the cell that flowed into the pipette (Lp) due to the mechanical properties of each individual cell. The Lp value was determined from microscopy images. Table 1 shows the Lp (μm) values and corresponding changes in electrical responses (electrical impedance (kΩ) and phase (θ)) for each single cell that was aspirated by three increasing various suction forces of F1, F2 and F3. These data shows that the average impedance and phase variation of an aspirated HT-29 cell were approximately 2-fold higher than those of a SW-48 cell.

TABLE 1

Change in cell electrical parameters due to the mechanical aspiration

| Cell type | Suction force | Lp (μm) | $\Delta Imp_{ave}$ (Ω) | $\Delta Phase_{ave}$ (°) |
|---|---|---|---|---|
| QU-DB | F1 | 4 | | |
| | F2 | 6 | 190.5 | 0.73 |
| | F3 | 8 | 88.2 | 0.52 |
| MRC-5 | F1 | 2.5 | | |
| | F2 | 4.5 | 2776.76 | 4.01 |
| | F3 | 5.8 | 2382.1 | 3.74 |
| SW-48 | F1 | 4.4 | | |
| | F2 | 6.7 | 133.4 | 0.71 |
| | F3 | 8.6 | 74.8 | 0.21 |
| HT-29 | F1 | 3.3 | | |
| | F2 | 5.4 | 272.1 | 1.46 |
| | F3 | 7.5 | 222.6 | 1.17 |

What is claimed is:

1. An electromechanical system for detecting cancerous state of a single cell, comprising:
   an aspirating mechanism configured to:
      extract a single cell from a suspension of a plurality of suspended biological cells;
      hold the extracted single cell; and
      apply a mechanical aspiration to the held single cell by applying a suction force to the held single cell;
   an electrical measurement mechanism, the electrical measurement mechanism configured to:
      apply a set of electrical signals to the single cell before and after applying the mechanical aspiration;
      measure a first set of electrical responses from the held single cell corresponding to the applied set of electrical signals before the mechanical aspiration; and
      measure a second set of electrical responses from the mechanically aspirated single cell corresponding to the applied set of electrical signals after the mechanical aspiration; and
   a processing mechanism comprising a data processor, the processing mechanism configured to detect cancerous state of the single cell based on a difference between the first set of electrical responses and the second set of electrical responses.

2. The electromechanical system of claim 1, wherein the set of electrical signals comprises a set of electrical voltages of 40 mV at a set of frequency values in a range between 100 Hz and 100 KHz.

3. The electromechanical system of claim 1, wherein each of the first set of electrical responses and the second set of electrical responses comprises a set of at least one of electrical impedance values, electrical phase values, and combinations thereof.

4. The electromechanical system of claim 3, wherein the data processor is configured to:
   receive the first set of electrical responses and the second set of electrical responses from the electrical measurement mechanism;
   calculate the difference between the first set of electrical responses and the second set of electrical responses by calculating a set of difference values between each two respective values of the first set of electrical responses and the second set of electrical responses; and
   detect the single cell to be cancerous responsive to the calculated difference between the first set of electrical responses and the second set of electrical responses being near zero.

5. The electromechanical system of claim 1, wherein the aspirating mechanism comprises:
   an electrically activated micropipette, comprising a nozzle at a first end of the electrically activated micropipette, configured to transfer the mechanical aspiration to the held single cell, the electrically activated micropipette configured to:
      extract the single cell from the suspension of the plurality of suspended biological cells;
      hold the extracted single cell; and
      act as an electrical ground potential for the electrical measurement mechanism; and
   a liquid reservoir connected to a second end of the electrically activated micropipette, the liquid reservoir configured to function a pressure source for the mechanical aspiration.

6. The electromechanical system of claim 5, wherein the electrically activated micropipette comprises:
a micropipette; and
an electrical conductive layer coated on outer surface of the nozzle, the electrical conductive layer comprising at least one of gold (Au), titanium (Ti), platinum (Pt), and combinations thereof.

7. The electromechanical system of claim 6, wherein the micropipette is made of at least one of glass, quartz, plastic, and combinations thereof.

8. The electromechanical system of claim 5, wherein:
the electrically activated glass micropipette is assembled on a microinjection microscope, and
the liquid reservoir comprises a movable water reservoir of the microinjection microscope, the movable water reservoir configured to move downward to supply a suction pressure for the mechanical aspiration.

9. The electromechanical system of claim 1, wherein the electrical measurement mechanism comprises:
an electrical probe, configured to connect to the held single cell; and
a signal controlling system connected to the electrical probe, the signal controlling system configured to:
apply an electrical signal to the held single cell via the electrical probe; and
acquire an electrical response corresponding to the applied electrical signal from the held single cell via the electrical probe.

10. The electromechanical system of claim 9, wherein the electrical probe comprises:
a tungsten microwire with a diameter less than 500 μm with a sharpened tip section, the sharpened tip section with a sharp pointed tip with a diameter of 200 nm or less;
a catalyst layer formed on the sharpened tip section of the tungsten microwire;
an array of nanotube electrodes vertically aligned on the catalyst layer, the nanotube electrodes comprising a plurality of doped silicon nanotubes (SiNTs) comprising a long free-end silicon nanotube located on the sharp pointed tip being longer than remaining SiNTs of the plurality of doped SiNTs; and
a gold layer coated over the plurality of doped SiNTs, wherein the long free-end silicon nanotube is configured to connect with and penetrate into the held single cell.

11. The electromechanical system of claim 10, wherein the catalyst layer comprises a catalyst bilayer comprising a nickel layer over a gold layer.

12. The electromechanical system of claim 11, wherein the catalyst layer comprises the nickel layer with a thickness in a range between 10 nm and 40 nm over the gold layer with a thickness in a range between 1 nm and 4 nm.

13. The electromechanical system of claim 10, wherein the gold layer coated over the plurality of doped SiNTs has a thickness of 5 nm or less.

14. The electromechanical system of claim 10, wherein the plurality of doped SiNTs comprises a plurality of doped SiNTs with phosphorus.

15. The electromechanical system of claim 9, wherein the electrical probe is assembled on a microinjection microscope.

16. The electromechanical system of claim 9, wherein the signal controlling system comprises:
an AC signal source, configured to apply the electrical signal to the electrical probe; and
a data acquisition module, configured to:
acquire the electrical response corresponding to the applied electrical signal from the electrical probe; and
send the electrical response to the data processor.

17. The signal controlling system of claim 16, wherein the AC signal source is configured to apply a voltage of 40 mV in a frequency range between 100 Hz and 100 KHz to the electrical probe.

18. The electromechanical system of claim 1, wherein the biological cells comprise a plurality of cells with elastic cell membranes, the cells comprising at least one of epithelial cells, endothelial cells, mesenchymal cells, and combinations thereof.

* * * * *